(12) United States Patent
Johnston

(10) Patent No.: US 10,900,975 B2
(45) Date of Patent: Jan. 26, 2021

(54) SYSTEMS AND METHODS OF EPITOPE BINNING AND ANTIBODY PROFILING

(71) Applicant: Arizona Board of Regents on behalf of Arizona State University, Scottsdale, AZ (US)

(72) Inventor: Stephen Albert Johnston, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 866 days.

(21) Appl. No.: 15/153,540

(22) Filed: May 12, 2016

(65) Prior Publication Data
US 2017/0131276 A1 May 11, 2017

Related U.S. Application Data

(60) Provisional application No. 62/160,276, filed on May 12, 2015.

(51) Int. Cl.
*G01N 33/68* (2006.01)

(52) U.S. Cl.
CPC .................. *G01N 33/6878* (2013.01)

(58) Field of Classification Search
None
See application file for complete search history.

(56) References Cited

U.S. PATENT DOCUMENTS

| 5,143,854 A | 11/1992 | Pirrung et al. |
| 5,969,108 A | 10/1999 | McCafferty et al. |
| 6,300,064 B1 | 10/2001 | Knappik et al. |

OTHER PUBLICATIONS

Wegner et al Analytical Chemistry 74:5161-8 (Year: 2002).*
Forsstrom et al Molecular & Cellular Proteomics 13:1585-97 (Year: 2014).*
Magnan et al Bioinformatics 26:2936-43 (Year: 2010).*
Stafford et al (Molecular & Cellular Proteomics 11:10.1074/mcp.M111.011593, 1-14, 2012) (Year: 2012).*
Brooks, The Importance of Epitope Binning for Biological Drug Discovery., Current Drug Discovery Technologies, 2014, 11(2):109-112.
Richer et al., Epitope Identification from Fixed-complexity Random-sequence Peptide Microarrays., Molecular & Cellular Proteomics, Jan. 2015, 14:136-47.
Rigoutsos et al., Combinatorial pattern discovery in biological sequences: The TEIRESIAS algorithm., Bioinformatics, 1998, 14(1):55-67.
Jonassen, Efficient discovery of conserved patterns using a pattern graph., Computer Applications in the Biosciences, 1997, 13(5):509-22.
Legutki et al., Scalable high-density peptide arrays for comprehensive health monitoring., Nature Communications, Sep. 2014, 5:4785(7 pages).
Chaddock et al., A new type of signal peptide: central role of a twin-arginine motif in transfer signals for the delta pH-dependent thylakoidal protein translocase., EMBO, Jun. 1995, 14(12):2715-22.
Bahler et al., Calmodulin signaling via the IQ motif., FEBS Letters, 2002, 513(1):107-13.
Halperin et al., Exploring antibody recognition of sequence space through random-sequence peptide microarrays., Molecular & Cellular Proteomics, Mar. 2011, 10(3):M110.000786(10 pages).
Garcia et al., Recognition of synthetic oligopeptides from nonstructural proteins NS1 and NS3 of dengue-4 virus by sera from dengue virus-infected children., American Journal of Tropical Medicine and Hygiene, 1997, 56(4):466-70.
Wagner et al., Antibodies to Borrelia burgdorferi OspA, OspC, OspF, and C6 Antigens as Markers for Early and Late Infection in Dogs., Clinical and Vaccine Immunology, 2012, 19(4):527-35.

* cited by examiner

*Primary Examiner* — Christopher M Gross
(74) *Attorney, Agent, or Firm* — Knobbe, Martens, Olson & Bear, LLP

(57) ABSTRACT

Methods for antibody profiling and epitope mapping are provided herein. More particularly, methods for screening and mapping epitopes of candidate antibodies and protein target identification are provided herein.

18 Claims, 15 Drawing Sheets

Specification includes a Sequence Listing.

Relative Binding (fraction of top sequence)

FIGURE 4A

Predictive VS Non-Predictive Subsequences

| HA Subsequences | | P53Ab8 Subsequences | |
|---|---|---|---|
| - PF- DAPV- | 14.5 | - - - - LNRYVE | 5.0 |
| - PF- DAP- - | 12.4 | - - - HLNCH - - | 4.3 |
| - RF- DAP- - | 31.0 | - - DHLVAP- - | 4.2 |
| - - - - DAPW | 12.4 | - - - HEKPR- - | 3.9 |
| - - - - DVPDG | 24.2 | - - NHLSHR- - | 4.1 |
| - - - - DVPD- | 24.2 | - - - - SDLWK- | 4.2 |
| - - - - DVPDR | 22.4 | - - - - SDLWKL | 4.1 |
| - - A- DVPD- | 35.5 | - - - - SDLW - | 4.4 |
| - - Y- DVPD- | 15.2 | - - - HHDKW- | 4.2 |
| - - - - DSPDE | 12.9 | - - GPNDLR- - | 4.1 |
| - - A- DAPD- | 16.1 | - - AHNHRP- - | 4.1 |
| - - Y- DAPD- | 20.2 | - - HHRHRP- - | 3.9 |
| - - Y- DAPGQ | 24.2 | - - VHPLRP- - | 4.3 |
| NQY- DAP- - | 16.0 | - - - HGLSLG | 3.9 |
| GPY- DAP- - | 28.3 | - - - H- LPLCK | 4.3 |
| APY- DAP- - | 14.2 | - SKHSWG - - | 4.3 |
| - PY- DAPE- | 16.1 | - GPHNCG - - | 4.1 |
| - GY- DAPE- | 15.6 | - - - HRREF- - | 4.4 |
| - - Y- DAPE- | 28.3 | PNPHDR- - - - | 3.9 |
| - - Y- DAPEW | 14.6 | - - - HSPHFN- | 4.1 |
| - - FEDW- - | 19.1 | - - - YVRHQA- | 4.3 |
| - - FYDVPE- | 16.1 | - - - SVSEQ - - | 3.9 |
| - - W DVPEA | 31.0 | - - - HPOADL- | 4.1 |
| - - Y- DVPE- | 17.9 | - - - HPSAE- - | 4.1 |
| - GY- DSPE- | 15.5 | - - - HPAALP- | 3.9 |
| - NY- DSPE- | 12.2 | - - - VPQGE- - | 4.3 |

SEQUENCE LISTING

```
<160> NUMBER OF SEQ ID NOS: 411

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg His Ser Val Val Asp
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg His Ser Val Val Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg His Ser Val Val
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg His Ser Val
1

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Val Arg His Ser Val
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                    peptide

<400> SEQUENCE: 6

Val Arg His Ser Val Val
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg His Ser Val Val Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Arg His Ser Val
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg His Ser Val Val Trp
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Ala Arg His Ser Val
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg His Ser Val Val
1               5

<210> SEQ ID NO 12
```

<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Arg His Ser Val
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Arg His Ser Val Val
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Arg His Ser Val
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Trp Gln Tyr Leu Pro
1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Val Tyr Pro Phe Ala Arg Gly Val Asp Pro Val Lys Asp
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

-continued

Trp Ala Trp Gln Leu Pro Val Arg Glu Gly Gln Lys
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Trp Val Ala Arg His Ser Val Val
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Leu Pro Ala Arg His Ser Val Val Asp
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp His Asp Ser Val Arg His Ser Val Val
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg His Ser Val Val
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Tyr Ala Arg His Ser Val Val Asp
1               5

<210> SEQ ID NO 23
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 23

Pro Val Arg His Ser Val Val Trp Asp
1               5

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp His Leu Trp Trp Arg Pro Gly Val Asp Trp Gly Trp
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Val Tyr Val Arg His Ser Val Val Gln Tyr His
1               5                   10

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Trp Pro His Gln Ser Leu His Leu Gly Asp Arg Asp Asp His
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Pro Asp Ser Arg His Ser Val Val His
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Trp Val Ala Val Arg His Ser Val Val His
1               5                   10
```

```
<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Leu Arg His Ser Val Val Lys Trp
1               5

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Tyr Ser Ala Arg Phe Ala Lys Ser Glu Arg Glu Phe Lys
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Asp Val Pro Asp
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Asp Ala Pro Asp
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Phe Asp Ala Pro Val
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

Phe Glu Asp Val Val
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Asp Ala Pro Gly Gln
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Val Pro Asp Gly
1               5

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Val Pro Asp
1

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Val Pro Asp Arg
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asn Gln Tyr Asp Ala Pro
1               5

<210> SEQ ID NO 40
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 40

Pro Phe Asp Ala Pro
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Ala Pro Val Val
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Tyr Asp Ala Pro Glu
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Pro Tyr Asp Ala Pro
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Asp Ala Pro Glu
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Tyr Asp Ala Pro Glu
1               5
```

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Pro Trp Pro Gln Glu Asp Leu Val Asp Asn Glu Lys
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Val Tyr Asn Glu Ala Asn Lys Arg Ser Tyr Phe Asp Trp
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Ala Asn Ser Gln Trp Glu
1               5

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Arg Phe Phe Tyr Asp Ala Pro Glu Gln Gly Gln Val Trp His
1               5                   10                  15

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Ala Gly Gln Glu Asp Asn Pro Asp Gly Asn
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 51

Trp Pro Ser Arg Lys Ala Asp Ala Pro Glu Glu Val
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Glu Asp Lys Pro Gly Glu Phe Val Trp
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Asp Asn Gly Tyr Asp Val Pro Asp Glu Trp Lys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Phe Glu Asp Asn Val Asp Gly Lys Asp
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Trp His Val Trp Phe Lys Tyr Asp Ala Pro Glu Asp Asn Phe
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Pro Ala Asp Val Asn Asp Arg Pro Glu Lys Val Leu Asp
1               5                   10

<210> SEQ ID NO 57
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 57

Val Tyr Asn Asp Ala Pro Glu Val Tyr Val Glu
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Phe Phe Asn Gln Asp Val Pro Asp Pro Lys
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Asn Phe Lys Pro Gly Trp Glu Asn Phe Val Pro Lys Asp
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Leu Asp Val Asn Asp Leu Pro Gln Gln Glu
1               5                   10

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Pro Asp Asn Val
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Phe Asp Ser Val Gly
1               5
```

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Pro Tyr Asp Val Gly
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Ala Asp Ser Lys
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Phe Asp Ser Val Gly Gly
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Tyr Asp Ser Arg Gly
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Tyr Asp Ser His Pro
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Asp Ser Lys Gly Val
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Ala Asp Ser Trp Pro
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Tyr Asp Ser His Gly
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Ser Arg Pro Gly Asp
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Phe Asp Ser Trp Gly
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asn Asp Ser Asn Pro Gly
1               5

<210> SEQ ID NO 74
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Asn Asp Ser Gly Gly
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Pro Asn Asp Ser Gly
1               5

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Leu Ala Ala Pro Tyr Asp Val Gly Asn Phe
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Val Ala Pro Pro Phe Glu Tyr Asp Ser Gln Gly Phe Glu
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Trp Pro Tyr Ser Ala Phe Asp Ser Leu Pro Gly Gln Asp
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Gly Pro Phe Asn Asp Ser His Val Glu Glu Phe Glu Leu
```

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Pro Ala Asp Ser Gly Pro Gln Leu Ser Glu Gly Trp
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Glu Pro Asn Asp Ser Asn Ser Leu Tyr Asn Phe
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Val Tyr Ala Pro Asn Asp Ser Gly Gly Glu
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Tyr Ala Pro Asn Asp Val Gln Tyr Pro Arg
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Asp Ser Trp Pro Gln Ala Asp Ser Glu Phe Lys
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Ala Tyr Pro Tyr Asp Ser Val Gly Leu Gly Gly Glu Trp
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Tyr Ser Gly Asn Asp Ser Val Ser Gly Val Tyr Asp Trp
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Ser Ala Val Gly Pro Phe Asp Ser Val Gly Gln Asp
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Tyr Trp Gly Asn Asp Ser Arg Pro Gly Glu
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Ala Asp Ser Val Gly Glu Arg Ser Arg Asn Leu
1               5                   10

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Gly Pro Asn Asp Val Gly Tyr Asp
1               5

<210> SEQ ID NO 91

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Tyr Pro Glu Asp
1

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Asp Tyr Gln Glu
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Asp Tyr Ala Glu
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu Asp Tyr Gln Glu
1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Tyr Val Glu Asp
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96
```

-continued

```
Lys Asp Gly Glu Ala Val
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asp Gly Glu Ala Val
1               5

<210> SEQ ID NO 98
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Ala Pro
1

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Gly His Ala Gly
1               5

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asp Gly Ala Gln
1

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asp Tyr Gln Glu
1

<210> SEQ ID NO 102
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 102

Asp Tyr Pro Glu Asp
1               5

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asp Tyr Pro Glu Ala
1               5

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Tyr Ala Glu Leu
1               5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu Lys Asp Gly Gly Leu
1               5

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Asp Tyr Val Glu Asp Gln Asn Phe Glu Leu
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Val Ala Val Gln Tyr Ala Asp Tyr Val Glu Asp Glu Tyr
1               5                   10
```

```
<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Trp Leu Val Ser His Trp Glu Leu Trp Val Leu Asp Pro Glu
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Tyr Val Glu Asp Leu Gly Val Leu Gln Lys Glu Lys Lys
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Leu Trp Pro Asn Glu Asn Arg Pro Gly Gly Asp Glu
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Ala Leu Glu Lys Asp Gly Asp Trp Glu Leu Asn
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Leu Pro Ala Asp Tyr Gln Asp Val Gly Leu Glu Lys Phe Glu
1               5                   10

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113
```

Ala Ala Leu Glu Lys Asp Gly Glu Asn Trp Ala Asp Glu Phe Val
1               5                   10                  15

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Trp Pro Val Trp Pro Trp Gln Glu Asn His Glu Asn Glu
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Ala Leu Glu Lys Asp Gly Asp Ala Asp Pro Glu Leu Trp
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Ala Leu Glu Lys Asp Gly Glu Asp Leu Val Ala Leu Ser
1               5                   10

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Tyr Trp Asp Pro Val Trp
1               5

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Ser Asn Asn Tyr Asn His Pro Gly Tyr Gln Phe
1               5                   10

<210> SEQ ID NO 119
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 119

Ala Ala Leu Glu Lys Asp Gly Glu Ala Asp Phe Glu Asp Asn Asp
1               5                   10                  15

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Tyr Pro Glu Asp Ala Leu Ser Asn Tyr Leu
1               5                   10

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Glu Lys Asp Asn
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Leu Glu Lys Asp Phe
1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Glu Leu Glu Lys Asp
1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

His Asn Gly Ser Leu Pro
1               5
```

```
<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

His Leu Glu Lys Gly Asp
1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Asp His Ala Ala Lys
1               5

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Leu Ser Trp Trp
1               5

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Asn Pro Pro Gly Arg
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

His Pro Pro Asp Pro
1               5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 130

Arg Pro Glu Leu Gln Tyr
1               5

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Leu Glu Lys Asp Tyr
1               5

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Val Phe His Asp Leu Ser
1               5

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Val His Gly Asp Lys
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Leu Ala Ala His Asn Ala
1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Val Lys Val Asp
1               5

<210> SEQ ID NO 136
<211> LENGTH: 14
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 136

Ala Tyr Val Asn Ala Ser Leu Ser Trp Trp Tyr Asn Pro Lys
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Trp Asp Val Trp Phe His Pro Gly Arg Lys Phe Trp
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Val Pro Asn Gln Ala Asp Leu Gly Tyr Leu Gln Glu
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Ala Val Phe Glu Trp Asp Arg Tyr Arg
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Pro Asp His Asn Asn Glu Asn Arg His Gly Glu Glu
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Pro Trp Pro Trp Ala Arg Asn Lys Leu Lys
1               5                   10
```

<210> SEQ ID NO 142
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Glu Pro Pro Asn His Tyr Ala Arg Arg Tyr Lys Trp Gln Leu
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

His Tyr Val His Phe Glu Arg Leu Glu Lys Asp Tyr
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Glu Asn Ala Ala Leu Glu Lys Asp Asn Gln Asp
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Val Trp Gly Asn Gly Asp Leu Gly Gly Gln Val Pro
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Leu Pro Ala Arg Asn Ser His Pro Val Tyr
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 147

Glu Asp Tyr Arg Phe Ala His Pro Tyr Lys Gly Val
1               5                   10

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Trp His Gly Asn Gln Val Ser Gly Asn
1               5

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

His Ala Tyr Ala Val Trp Asn Arg Val Ser Leu Gln Gln Glu Trp
1               5                   10                  15

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Pro Tyr Ala Asn Trp Glu Arg Val Asp Arg Tyr Pro Asn
1               5                   10

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Ser Ala Phe Gln Glu
1               5

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Pro Asp Phe Phe Gln
1               5

<210> SEQ ID NO 153
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Ala Trp Pro Leu
1               5

<210> SEQ ID NO 154
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Glu Phe Asp Gly
1

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Trp Glu Asp Ala Lys Pro
1               5

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Tyr Ser Ala Gln Glu Ala
1               5

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asn Gln Glu Ala Ser Pro
1               5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asp Phe Asn Ala Pro
```

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Glu Asp Val Ala Trp Pro
1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Glu Ala Ser Tyr
1               5

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Glu Asp Phe Asn Ala
1               5

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Pro Trp Glu Asp Ala
1               5

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Val Ser Trp Ser
1               5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Trp Gln Glu Asp Ala Asn
1               5

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Trp Gln Glu Tyr Asp
1               5

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Asp Ala Ala Ala Ala Asp Ala Ser Tyr Asp Gly Glu
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Glu Asp Ala Ala Trp Pro Leu Asn Pro Glu
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Glu Asp Ala Trp Ala Ser Leu Pro Asp Gln Val
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Glu Asp Ser Val Pro Phe Gln Glu Ala Gly Trp Asn
1               5                   10

<210> SEQ ID NO 170

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asp Val Ala Glu Ala Ser Lys Pro Trp Glu
1               5                   10

<210> SEQ ID NO 171
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asp Ser Ala Phe Gln Tyr Ala Glu Gln Glu Phe Pro Tyr
1               5                   10

<210> SEQ ID NO 172
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Glu Ser Ala Ala Trp Phe Glu Leu Pro Gly Glu Glu Asn
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Asp Val Gln Glu Ala Arg Val Gln Asp Glu
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asp Ala Asp Trp Asn Gln Asn Pro Glu Leu Asp
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175
```

```
Glu Trp Ser Val Asn Trp Gln Glu Ala Val Asp Glu
1               5                   10
```

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

```
Asp Ala Ser Ala Ala Trp Ala Gly Glu Leu Gln Glu
1               5                   10
```

<210> SEQ ID NO 177
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

```
Glu Asp Val Ala Trp Pro Phe Gln Leu Gln Asn Glu
1               5                   10
```

<210> SEQ ID NO 178
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

```
Asp Ala Trp Asn Val Pro Ser Glu Leu Gly Tyr Gln Leu
1               5                   10
```

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

```
Ser Asn Gln Glu Ala Ser Gly Glu Gly Gln
1               5                   10
```

<210> SEQ ID NO 180
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Ser Val Gly Glu Asp Ala Ser Trp Trp Glu Gly Glu Phe Leu
1               5                   10
```

<210> SEQ ID NO 181
<211> LENGTH: 6
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 181

Leu Asn Arg Tyr Trp Glu
1               5

<210> SEQ ID NO 182
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

His Glu Lys Pro Arg
1               5

<210> SEQ ID NO 183
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Val His Pro Leu Arg Pro
1               5

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ser Lys His Ser Trp Gly
1               5

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Tyr Val Arg His Gln Ala
1               5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp His Leu Val Ala Pro
1               5

```
<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

His Pro Gln Ala Asp Leu
1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asn His Leu Ser His Arg
1               5

<210> SEQ ID NO 189
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

His Pro Ser Ala Glu
1               5

<210> SEQ ID NO 190
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

His Ser Pro His Phe Asn
1               5

<210> SEQ ID NO 191
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Pro His Asn Gly Gly
1               5

<210> SEQ ID NO 192
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192
```

```
Gly Pro Asn Asp Leu Arg
1               5

<210> SEQ ID NO 193
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Asp Leu Trp Lys
1               5

<210> SEQ ID NO 194
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Asp Leu Trp
1

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ser Asp Leu Trp Lys Leu Asp
1               5

<210> SEQ ID NO 196
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Glu Pro Ala Asp Pro Phe Leu Asn Pro Pro Lys Phe His Lys
1               5                   10

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Asp Tyr Trp Arg His His Gln Arg Asn Arg Gly Val Tyr Lys Pro
1               5                   10                  15

<210> SEQ ID NO 198
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 198

Tyr Ser Asp Leu Leu Lys Leu Gln Gly Trp Glu Trp
1               5                   10

<210> SEQ ID NO 199
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Pro Tyr Val Pro Tyr Pro Ser Glu Val Leu Gly Asp Arg
1               5                   10

<210> SEQ ID NO 200
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Glu Leu Asp Trp Gly Leu Val Glu Trp Lys Arg Val Leu Ser
1               5                   10

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Val His Phe Gly Pro Ser Gln Glu His
1               5

<210> SEQ ID NO 202
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Gly Pro Asn Phe Phe Glu Leu Asn Lys Gly Gln Gly Glu
1               5                   10

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

His Val Phe Gln Asp His Arg Pro Gly Val Gln Asp Trp Tyr Phe
1               5                   10                  15
```

<210> SEQ ID NO 204
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Trp Leu Pro Ala Gly Pro Asn Lys Gln Gly Leu Lys Glu Gly
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

His Leu Pro Val Ala Trp His Pro Lys Gln Arg Glu
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asn His Phe Lys Glu Ala Leu Gly Leu Tyr Lys
1               5                   10

<210> SEQ ID NO 207
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Glu Asp Pro Ala Ala Leu Asn Arg Arg Ser Gly Asn Lys
1               5                   10

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Glu Ala Pro Phe Gln Ala Arg Pro Gly Val Gln Trp Arg Asp Lys
1               5                   10                  15

<210> SEQ ID NO 209
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 209

His Tyr Ser Trp Phe Tyr Asp Arg Ser Gly Tyr Asn Arg
1               5                   10

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Pro Ser Ala His Pro Gln Ala Asp Leu His Arg Val Gly Pro Val
1               5                   10                  15

<210> SEQ ID NO 211
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Pro Trp His Trp Tyr
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Tyr Ser Arg Arg Gly Leu
1               5

<210> SEQ ID NO 213
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Arg Lys Leu Gln Arg
1               5

<210> SEQ ID NO 214
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Arg Lys Leu Gln Arg
1               5

<210> SEQ ID NO 215
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 215

Val Tyr Ala Lys Gly
1               5

<210> SEQ ID NO 216
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Val Asp Trp Lys Tyr
1               5

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Gln Tyr Ala Lys
1               5

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Pro Phe Arg Ser Leu Arg
1               5

<210> SEQ ID NO 219
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Phe Arg Leu Arg Val Gly
1               5

<210> SEQ ID NO 220
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Trp Arg Leu Ser
1               5
```

<210> SEQ ID NO 221
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Phe Arg Lys Arg Val Arg
1               5

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Arg Arg Lys Pro Arg
1               5

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Arg Lys Pro Arg Trp Gly
1               5

<210> SEQ ID NO 224
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Arg Phe Phe Ala Ser
1               5

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Arg Val Leu Arg Gln
1               5

<210> SEQ ID NO 226
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Glu Val Ala Pro Trp Leu Val Arg Glu Val Leu Lys Val Asn
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asp Ala Arg Trp Phe Asn Gln Ala Asp Arg Pro Pro Tyr Arg
1               5                   10

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Trp Pro His His Tyr Leu Val Gly Arg Tyr
1               5                   10

<210> SEQ ID NO 229
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Glu Leu Pro Val Asn His Gln His Pro Arg Glu Gly Asp
1               5                   10

<210> SEQ ID NO 230
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Trp Arg Phe Asn Lys Pro Arg Glu Val Trp Glu Asp
1               5                   10

<210> SEQ ID NO 231
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

His Val Ala Ala Phe Tyr Ala Leu Lys Trp His Trp
1               5                   10

<210> SEQ ID NO 232
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Asp Leu Tyr Leu Arg Pro Gln Lys Gly Glu His
1               5                   10

<210> SEQ ID NO 233
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Pro Asp Val Arg Gly Asn Trp Ala Gln Arg Glu Lys
1               5                   10

<210> SEQ ID NO 234
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Trp Leu Ala Tyr Arg Glu Gly Trp Tyr Asp Leu
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ala Val Asn Trp Gln Ser Lys Ser Tyr Trp Val Lys
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Pro Val His Pro Gly Leu Val Pro Ser Trp Gly Asp Tyr Glu
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Arg Phe Asn His Tyr Lys Ser Gly Glu Gln Asp Leu
```

<210> SEQ ID NO 238
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Glu Ala Asp Ser Trp Arg His Phe Asp Arg Leu Arg Pro
1               5                   10

<210> SEQ ID NO 239
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Tyr Ala Ala Phe Asn Lys Pro Gly Trp Glu Val
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Asp His Leu His Asn Trp Asn Arg Gly Gly Trp Arg Pro Arg
1               5                   10

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Tyr Pro Tyr Asp Val Pro Asp Tyr Ala
1               5

<210> SEQ ID NO 242
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Ala Leu Glu Lys Asp Tyr Glu Glu Val Gly Val
1               5                   10

<210> SEQ ID NO 243
<211> LENGTH: 8
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 243

Thr Phe Arg His Ser Val Val Val
1               5

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asp Tyr Lys Asp Asp Asp Asp Lys
1               5

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln Ala Phe Asp Ser His Tyr
1               5

<210> SEQ ID NO 246
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Glu Glu Asp Phe Arg Val
1               5

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Thr Phe Ser Asp Leu Trp Lys Leu Leu Pro Glu
1               5                   10

<210> SEQ ID NO 248
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asn Ala His Tyr Tyr Val Phe Phe Glu Glu Gln Glu
1               5                   10

<210> SEQ ID NO 249

```
<211> LENGTH: 5
<212> TYPE: PRT
<213> ORGANISM: Dengue virus

<400> SEQUENCE: 249

Ala Val His Ala Asp
1               5

<210> SEQ ID NO 250
<211> LENGTH: 4
<212> TYPE: PRT
<213> ORGANISM: Dengue virus

<400> SEQUENCE: 250

Ala Val His Ala
1

<210> SEQ ID NO 251
<211> LENGTH: 4
<212> TYPE: PRT
<213> ORGANISM: Dengue virus

<400> SEQUENCE: 251

Val His Ala Asp
1

<210> SEQ ID NO 252
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ser Asp Leu Trp Lys Leu
1               5

<210> SEQ ID NO 253
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gln Ala Phe Asp Ser His
1               5

<210> SEQ ID NO 254
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Arg His Ser Val Val
1               5

<210> SEQ ID NO 255
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 255

Ala Ala Leu Glu Lys Asp
1               5

<210> SEQ ID NO 256
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asp Val Pro Asp
1

<210> SEQ ID NO 257
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Phe Asp Ser His
1

<210> SEQ ID NO 258
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Asp Tyr Asp Asp Asp Lys
1               5

<210> SEQ ID NO 259
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ala Leu Glu Lys Asp
1               5

<210> SEQ ID NO 260
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ala Leu Glu Lys Asp Tyr
1               5
```

```
<210> SEQ ID NO 261
<211> LENGTH: 5
<212> TYPE: PRT
<213> ORGANISM: Dengue virus

<400> SEQUENCE: 261

Arg Glu Gly Glu Lys
1               5

<210> SEQ ID NO 262
<211> LENGTH: 5
<212> TYPE: PRT
<213> ORGANISM: Treponema pallidum

<400> SEQUENCE: 262

Asp Tyr Ala Phe Gly
1               5

<210> SEQ ID NO 263
<211> LENGTH: 4
<212> TYPE: PRT
<213> ORGANISM: Borrelia burgdorferi

<400> SEQUENCE: 263

Glu Asp Ala Lys
1

<210> SEQ ID NO 264
<211> LENGTH: 4
<212> TYPE: PRT
<213> ORGANISM: Bordetella pertussis

<400> SEQUENCE: 264

Phe Lys Glu Gly
1

<210> SEQ ID NO 265
<211> LENGTH: 5
<212> TYPE: PRT
<213> ORGANISM: Plasmodium falciparum

<400> SEQUENCE: 265

Ser Asn Lys Gln Gly
1               5

<210> SEQ ID NO 266
<211> LENGTH: 5
<212> TYPE: PRT
<213> ORGANISM: Plasmodium falciparum

<400> SEQUENCE: 266

Arg Leu Lys Glu Pro
1               5

<210> SEQ ID NO 267
<211> LENGTH: 5
<212> TYPE: PRT
<213> ORGANISM: Plasmodium falciparum

<400> SEQUENCE: 267

Asp Ala Phe Glu Tyr
1               5

<210> SEQ ID NO 268
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (7)..(7)
<223> OTHER INFORMATION: Any amino acid

<400> SEQUENCE: 268

Gly Asn Xaa Ala Ala Leu Xaa Leu
1               5

<210> SEQ ID NO 269
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Tyr Asp Val Pro Asp
1               5

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Asp Tyr Asp Asp Asp Asp Lys
1               5

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ala Ala Leu Glu Lys Asp Tyr
1               5

<210> SEQ ID NO 272
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Pro Phe Asp Ala Pro Val
1               5

<210> SEQ ID NO 273
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 273

Pro Phe Asp Ala Pro
1               5

<210> SEQ ID NO 274
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Arg Phe Asp Ala Pro
1               5

<210> SEQ ID NO 275
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Asp Ala Pro Val Val
1               5

<210> SEQ ID NO 276
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Asp Val Pro Asp Gly
1               5

<210> SEQ ID NO 277
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Asp Val Pro Asp
1

<210> SEQ ID NO 278
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Asp Val Pro Asp Arg
1               5
```

<210> SEQ ID NO 279
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ala Asp Val Pro Asp
1               5

<210> SEQ ID NO 280
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Tyr Asp Val Pro Asp
1               5

<210> SEQ ID NO 281
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Asp Ser Pro Asp Glu
1               5

<210> SEQ ID NO 282
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ala Asp Ala Pro Asp
1               5

<210> SEQ ID NO 283
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Tyr Asp Ala Pro Asp
1               5

<210> SEQ ID NO 284
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Tyr Asp Ala Pro Gly Gln
1               5

<210> SEQ ID NO 285
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Asn Gln Tyr Asp Ala Pro
1               5

<210> SEQ ID NO 286
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gly Pro Tyr Asp Ala Pro
1               5

<210> SEQ ID NO 287
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ala Pro Tyr Asp Ala Pro
1               5

<210> SEQ ID NO 288
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Pro Tyr Asp Ala Pro Glu
1               5

<210> SEQ ID NO 289
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gly Tyr Asp Ala Pro Glu
1               5

<210> SEQ ID NO 290
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Tyr Asp Ala Pro Glu
1               5

<210> SEQ ID NO 291
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Tyr Asp Ala Pro Glu Trp
1               5

<210> SEQ ID NO 292
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Phe Glu Asp Val Val
1               5

<210> SEQ ID NO 293
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Phe Tyr Asp Val Pro Glu
1               5

<210> SEQ ID NO 294
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Trp Asp Val Pro Glu Ala
1               5

<210> SEQ ID NO 295
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Tyr Asp Val Pro Glu
```

```
1               5

<210> SEQ ID NO 296
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Gln Tyr Asp Ser Pro Glu
1               5

<210> SEQ ID NO 297
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Asn Tyr Asp Ser Pro Glu
1               5

<210> SEQ ID NO 298
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Leu Asn Arg Tyr Trp Glu
1               5

<210> SEQ ID NO 299
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

His Leu Asn Gln His
1               5

<210> SEQ ID NO 300
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Asp His Leu Val Ala Pro
1               5

<210> SEQ ID NO 301
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 301

His Glu Lys Pro Arg
1               5

<210> SEQ ID NO 302
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Asn His Leu Ser His Arg
1               5

<210> SEQ ID NO 303
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ser Asp Leu Trp Lys
1               5

<210> SEQ ID NO 304
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ser Asp Leu Trp Lys Leu
1               5

<210> SEQ ID NO 305
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ser Asp Leu Trp
1

<210> SEQ ID NO 306
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

His His Asp Lys Trp
1               5

<210> SEQ ID NO 307

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gly Pro Asn Asp Leu Arg
1               5

<210> SEQ ID NO 308
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ala His Asn His Arg Pro
1               5

<210> SEQ ID NO 309
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

His His Arg His Arg Pro
1               5

<210> SEQ ID NO 310
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Val His Pro Leu Arg Pro
1               5

<210> SEQ ID NO 311
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

His Gly Leu Ser Leu Gly
1               5

<210> SEQ ID NO 312
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312
```

His Leu Pro Leu Gln Lys
1               5

<210> SEQ ID NO 313
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ser Lys His Ser Trp Gly
1               5

<210> SEQ ID NO 314
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Pro His Asn Gly Gly
1               5

<210> SEQ ID NO 315
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

His Arg Arg Glu Phe
1               5

<210> SEQ ID NO 316
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Pro Asn Pro His Asp Arg
1               5

<210> SEQ ID NO 317
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

His Ser Pro His Phe Asn
1               5

<210> SEQ ID NO 318
<211> LENGTH: 6
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 318

Tyr Val Arg His Gln Ala
1               5

<210> SEQ ID NO 319
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Ser Val Ser Glu Gln
1               5

<210> SEQ ID NO 320
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

His Pro Gln Ala Asp Leu
1               5

<210> SEQ ID NO 321
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

His Pro Ser Ala Glu
1               5

<210> SEQ ID NO 322
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

His Pro Ala Ala Leu Pro
1               5

<210> SEQ ID NO 323
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Val Pro Gln Gly Glu
1               5
```

```
<210> SEQ ID NO 324
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Ala Val His Ala Asp
1               5

<210> SEQ ID NO 325
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Ala Val His Glu Gly
1               5

<210> SEQ ID NO 326
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Ala Val His Glu Tyr
1               5

<210> SEQ ID NO 327
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Val Pro His Phe Glu Asp
1               5

<210> SEQ ID NO 328
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Glu Arg Lys Phe Glu
1               5

<210> SEQ ID NO 329
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329
```

Ala Val His Asn Glu
1               5

<210> SEQ ID NO 330
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ala Val His Phe Glu Ala
1               5

<210> SEQ ID NO 331
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ala Pro His Gln Glu Ala
1               5

<210> SEQ ID NO 332
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Asn Glu Gly Leu Gly Glu
1               5

<210> SEQ ID NO 333
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Pro His Phe Glu Asp Pro
1               5

<210> SEQ ID NO 334
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Asp Tyr Ala Phe Gly
1               5

<210> SEQ ID NO 335
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 335

Asp Tyr Ala Trp Phe Ala Lys
1               5

<210> SEQ ID NO 336
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Asp Tyr Ala Ala Lys
1               5

<210> SEQ ID NO 337
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Asp Tyr Ala Pro Phe Glu
1               5

<210> SEQ ID NO 338
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Asp Tyr Ala Trp Ser
1               5

<210> SEQ ID NO 339
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Asp Tyr Ser Val Lys Gln
1               5

<210> SEQ ID NO 340
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Tyr Ala Val Trp Gly Asp
1               5
```

-continued

<210> SEQ ID NO 341
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Asp Tyr Ala Ala Gly Pro
1               5

<210> SEQ ID NO 342
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Asp Tyr Ala Val Lys
1               5

<210> SEQ ID NO 343
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Asp Tyr Ala Ala Pro Gly
1               5

<210> SEQ ID NO 344
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Phe Lys Glu Gly Asp
1               5

<210> SEQ ID NO 345
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Arg Phe Lys Glu Gly Asp
1               5

<210> SEQ ID NO 346
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 346

Glu Ser Lys Pro Glu
1               5

<210> SEQ ID NO 347
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Pro Phe Lys Glu Gly Asp
1               5

<210> SEQ ID NO 348
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

His Phe Lys Glu Gly Asp
1               5

<210> SEQ ID NO 349
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Phe Phe Lys Glu Gly Asp
1               5

<210> SEQ ID NO 350
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Ser Lys Pro Glu Gly Val
1               5

<210> SEQ ID NO 351
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Trp Trp Lys Gln Gly Asp
1               5

<210> SEQ ID NO 352
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 352

Phe Lys Glu Gly Asp Ser
1               5

<210> SEQ ID NO 353
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ser Asn Lys Gln Gly
1               5

<210> SEQ ID NO 354
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Asp Ser Asn Lys Gln
1               5

<210> SEQ ID NO 355
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Ser Asn Lys Gln Asp
1               5

<210> SEQ ID NO 356
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ala Asp Gly Phe Glu Tyr
1               5

<210> SEQ ID NO 357
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Asp Ala Phe Glu Tyr
1               5
```

```
<210> SEQ ID NO 358
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Asn Lys Gln Glu Gly Asp
1               5

<210> SEQ ID NO 359
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Ser Trp Lys Gln Gly
1               5

<210> SEQ ID NO 360
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Ser Asn Lys Gln His
1               5

<210> SEQ ID NO 361
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Asp Ser Trp Lys Gln
1               5

<210> SEQ ID NO 362
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ser Asn Lys Gln Ala
1               5

<210> SEQ ID NO 363
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 363

Glu Gly Glu Lys Val
1               5

<210> SEQ ID NO 364
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Pro Glu Gly Glu Lys
1               5

<210> SEQ ID NO 365
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Glu Gly Glu Lys Gly
1               5

<210> SEQ ID NO 366
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Glu Gly Glu Lys Glu
1               5

<210> SEQ ID NO 367
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Leu Glu Gly Glu Lys
1               5

<210> SEQ ID NO 368
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Asn Glu Gly Glu Lys Gly
1               5

<210> SEQ ID NO 369
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Glu Gly Glu Lys Asp
1               5

<210> SEQ ID NO 370
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Glu Gly Glu Lys
1

<210> SEQ ID NO 371
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

His Val Glu Gly Glu Lys
1               5

<210> SEQ ID NO 372
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Pro Glu Gly Glu Lys Pro
1               5

<210> SEQ ID NO 373
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Arg Glu Gly Glu Lys
1               5

<210> SEQ ID NO 374
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Glu Asp Trp Lys Gln
```

```
1               5
```

```
<210> SEQ ID NO 375
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Glu Asp Leu Lys Gln
1               5

<210> SEQ ID NO 376
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Glu Asp Asn Lys Glu
1               5

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Glu Asp Ala His Gly Phe Lys
1               5

<210> SEQ ID NO 378
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Glu Asp Ser Lys
1

<210> SEQ ID NO 379
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Glu Asp Asn Lys Arg
1               5

<210> SEQ ID NO 380
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 380

Glu Asp Ala Lys Gln
1               5

<210> SEQ ID NO 381
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Glu Asp Arg Lys Glu
1               5

<210> SEQ ID NO 382
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Glu Asp Lys His
1

<210> SEQ ID NO 383
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Glu Asp Ala Lys Ala
1               5

<210> SEQ ID NO 384
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Glu Asp Ala Lys
1

<210> SEQ ID NO 385
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Asn Gln Gly Tyr Ala Arg
1               5

<210> SEQ ID NO 386

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ala Leu Arg Tyr Gln Gly
1               5

<210> SEQ ID NO 387
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ser Gly Gln Arg Gly
1               5

<210> SEQ ID NO 388
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gly Ser Arg Val Leu
1               5

<210> SEQ ID NO 389
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Arg Val Leu Asp Arg Gly
1               5

<210> SEQ ID NO 390
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Ala Arg Arg Glu Leu
1               5

<210> SEQ ID NO 391
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391
```

Arg Leu Lys Glu Pro
1               5

<210> SEQ ID NO 392
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Arg Leu Ser Pro Glu Arg
1               5

<210> SEQ ID NO 393
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Glu Asp Ala Pro Phe Ala
1               5

<210> SEQ ID NO 394
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Ser Asn Lys Gln
1

<210> SEQ ID NO 395
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

His Ser Asn Lys Gln
1               5

<210> SEQ ID NO 396
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Ser Asn Lys Gln His
1               5

<210> SEQ ID NO 397
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 397

Asp Ser Asn Lys Gln
1               5

<210> SEQ ID NO 398
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Ser Asn Lys Gln Gly
1               5

<210> SEQ ID NO 399
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Glu Ser His Lys Gln
1               5

<210> SEQ ID NO 400
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Asn Lys Gln Glu Gly Asp
1               5

<210> SEQ ID NO 401
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Ser Trp Lys Gln Gly
1               5

<210> SEQ ID NO 402
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Asp Ser Trp Lys Gln
1               5
```

```
<210> SEQ ID NO 403
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Asn Ser Phe His
1

<210> SEQ ID NO 404
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Asp Gly Phe Glu Tyr
1               5

<210> SEQ ID NO 405
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Ala Asp Gly Phe Glu Tyr
1               5

<210> SEQ ID NO 406
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Asp Ala Phe Glu Tyr
1               5

<210> SEQ ID NO 407
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Ala Asp Ala Asn Glu Tyr
1               5

<210> SEQ ID NO 408
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408
```

```
Lys Pro Val Trp Lys Gly Ser
1               5

<210> SEQ ID NO 409
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Arg His Pro Trp Tyr Gln Gly
1               5

<210> SEQ ID NO 410
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Lys Arg Pro Trp Tyr Gly Ser
1               5

<210> SEQ ID NO 411
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Ala Pro Trp Phe Pro
1               5
```

SYSTEMS AND METHODS OF EPITOPE BINNING AND ANTIBODY PROFILING

CROSS-REFERENCE

This application claims the benefit of U.S. Provisional Application No. 62/160,276, filed on May 12, 2015, which is entirely incorporated herein by reference.

SEQUENCE LISTING

The instant application contains a Sequence Listing which has been submitted electronically in ASCII format and is hereby incorporated by reference in its entirety. Said ASCII copy, created on Oct. 21, 2016, is named 43638-719_201_SL.txt and is 88,132 bytes in size.

BACKGROUND

This invention relates to methods and systems for developing therapeutic affinity reagents. More particularly, the present invention provides methods and systems for epitope mapping and monoclonal antibody profiling.

Antibodies play a central role in the immune system and in modern health care and medical research. They are commonly used as affinity reagents in research and diagnostic applications and have emerged as an important class of therapeutics. In particular, the development of monoclonal antibody (mAb) technology has had a profound impact on medicine. The therapeutic use of first-generation mAb achieved considerable success in the treatment of major diseases, including cancer, inflammation, autoimmune, cardiovascular, and infectious diseases. It is estimated that the majority of newly developed drugs will be biologics which include monoclonal antibodies.

The process of developing a monoclonal therapeutic starts with creating hundreds of hybridomas, each producing a different antibody, and screening pools of several monoclonal antibodies to identify monoclonals that recognize different sites on the target protein (epitopes) and that affect the target protein in the desired fashion. Unfortunately, standard methods developed for mapping antibody epitopes, including peptide tiling and phage, bacteria, and mRNA display, require costly synthesis or enrichment steps. At present, no low-cost universal platform for screening monoclonal antibodies exists. Therefore, there remains a need in the art for cost-effective and efficient methods and systems for monoclonal antibody profiling and epitope mapping.

SUMMARY OF THE INVENTION

Disclosed herein are methods for screening and characterizing antibody binding affinity and specificity to an antigen, including monoclonal antibodies. In general, the method comprises the steps of (a) contacting a sample comprising a monoclonal antibody having unknown specificity for an antigen of interest to a plurality of randomly generated peptides immobilized on a support; (b) selecting for peptides of the plurality that bind to the antibody; (c) screening the selected peptides to identify those that bind most strongly to the antibody; (d) deriving peptide sequences for the identified peptides; and (e) identifying among the derived peptide sequences a conserved motif, where the motif corresponds to an epitope of the antigen to which the monoclonal antibody specifically binds. Identifying among the derived peptide sequences can comprise using a search algorithm to search for a conserved motif. The peptide sequences can be from a database of amino acid sequences. The sample can be a hybridoma culture supernatant. The plurality of random-sequence peptide array can comprise at least 300,000 random-sequence peptides per 0.5 cm$^2$. Screening of the selected peptides for those that bind most strongly to the antibody can comprise an immunofluorescence assay. Identifying a consensus sequence can comprise aligning the sequences of said antigens using a search algorithm. The antibody can be a monoclonal antibody.

In some instances, the method further comprises identifying a protein target of the antibody, where identifying comprises searching a protein database for proteins that contain homologous sequences to the consensus sequence motif and retrieving those proteins from the database comparing the one or more consensus motifs to an amino acid sequence database, and verifying that the antibody binds to a protein retrieved from the database search.

Described herein, in some embodiments, are methods of identifying an epitope recognized by an antibody, the method comprising the steps of (a) contacting a sample comprising the antibody to a plurality of peptides immobilized on an array; (b) identifying peptides that bind to the antibody with a K$_d$ of less than 10$^{-7}$ M; and (c) screening the peptide sequences of the identified peptides for a consensus sequence motif, wherein the motif corresponds to an epitope of the antigen to which the antibody specifically binds. In some embodiments, screening the peptide sequences of the identified peptides for a consensus sequence motif comprises using a search algorithm. In some embodiments, the peptide sequences are from a database of amino acid sequences. In some embodiments, the peptides are randomly generated. In some embodiments, the array comprises at least 10,000 peptide features per 1 cm$^2$. In some embodiments, the array comprises at least 300,000 peptide features per 0.5 cm$^2$. In some embodiments, the peptides have a length of 1 to 25 amino acids. In some embodiments, identifying peptides that bind to the antibody comprises an immunofluorescence assay. In some embodiments, screening the peptide sequences of the identified peptides for a consensus sequence motif comprises aligning the peptide sequences using a search algorithm. In some embodiments, the number of peptide sequences screened is at least 500. In some embodiments, the antibody is a monoclonal antibody. In some embodiments, the sample is a hybridoma culture supernatant. In some embodiments, the sample is a serum sample. In some embodiments, the serum sample is from a vertebrate. In some embodiments, the serum sample is from a mammal. In some embodiments, the serum sample is from a human. In some embodiments, the serum sample comprises an antibody that recognizes an epitope in an antigen from an infectious organism. In some embodiments, the infectious organism is a pathogen. In some embodiments, the infectious organism is selected from the group consisting of viruses, bacteria, and protists. In some embodiments, the pathogen is *Borrelia*, *Bordetella*, hepatitis B virus, *Plasmodium*, *Treponema*, or dengue virus.

In some embodiments, the method further comprises identifying a protein target of the antibody, comprising (i) searching a protein sequence database for proteins that contain sequences homologous to the consensus sequence motif; (ii) identifying proteins from step (i); and (iii) verifying that the antibody binds to a protein retrieved from the database search. In some embodiments, homologous sequences show at least 80% identity. In some embodiments, the database comprises proteomes from bacteria, viruses, and eukaryotes. In some embodiments, the eukaryotes are protists. In some embodiments, the bacteria, viruses, and protists are pathogenic. In some embodiments, the identified peptide sequences binding to the antibody are hierarchically clustered and aligned. In some embodiments, the method further comprises examining peptides on the array that are not bound to antibody.

Disclosed herein are methods for characterizing the binding specificity of an antibody, the method comprising the steps of: (a) contacting a sample comprising the antibody to a plurality of peptides immobilized on an array; (b) identifying peptides that bind to the antibody with a $K_d$ of less than $10^{-7}$ M; (c) identifying peptides on the array that do not bind to the antibody; and (d) clustering and aligning the identified peptides from (b) and (c) to determine the level of specific binding recognized by the antibody. In some embodiments, the antibody is a monoclonal antibody. In some embodiments, the identified peptides are clustered by similarity of the identified peptides in (b) and (c) to the eliciting peptide used to make the monoclonal antibody. In some embodiments, the identified peptides are hierarchically clustered and aligned. In some embodiments, the level of similarity of identified peptides in steps (b) and (c) to the eliciting peptide is indicative of the degree of promiscuity of antibody binding. In some embodiments, the peptide sequences are from a database of amino acid sequences. In some embodiments, the peptides are randomly generated. In some embodiments, the array comprises at least 10,000 peptide features per 1 $cm^2$. In some embodiments, the array comprises at least 300,000 peptide features per 0.5 $cm^2$. In some embodiments, the peptides have a length of 1 to 25 amino acids. In some embodiments, identifying peptides that bind to the antibody comprises an immunofluorescence assay.

In some embodiments, screening the peptide sequences of the identified peptides binding to an antibody in step (b) further comprises determining a consensus sequence motif comprises aligning the peptide sequences using a search algorithm. In some embodiments, determining the consensus sequence comprises aligning the identified peptide sequences using a search algorithm. In some embodiments, the number of peptide sequences screened is at least 500. In some embodiments, the sample is a hybridoma culture supernatant. In some embodiments, the sample is a serum sample. In some embodiments, the serum sample is from a vertebrate. In some embodiments, the serum sample is from a mammal. In some embodiments, the serum sample is from a human. In some embodiments, the serum sample comprises an antibody that recognizes an epitope in an antigen from an infectious organism. In some embodiments, the infectious organism is a pathogen. In some embodiments, the infectious organism is selected from the group consisting of viruses, bacteria, and protists. In some embodiments, the pathogen is *Borrelia, Bordetella*, hepatitis B virus, *Plasmodium, Treponema*, or dengue virus.

These and other features, aspects, and advantages will become better understood upon consideration of the following detailed description, drawings, and appended claims.

BRIEF DESCRIPTION OF THE DRAWINGS

FIG. 4A illustrates sequence representation and predictive versus non-predictive subsequences. The top 25 sequence motifs found for the monoclonal antibodies HA (left) (SEQ ID NOS 272-297, respectively, in order of appearance) and p53 (right) (SEQ ID NOS 298-323, respectively, in order of appearance) are shown.

DETAILED DESCRIPTION OF THE INVENTION

Figure 1:
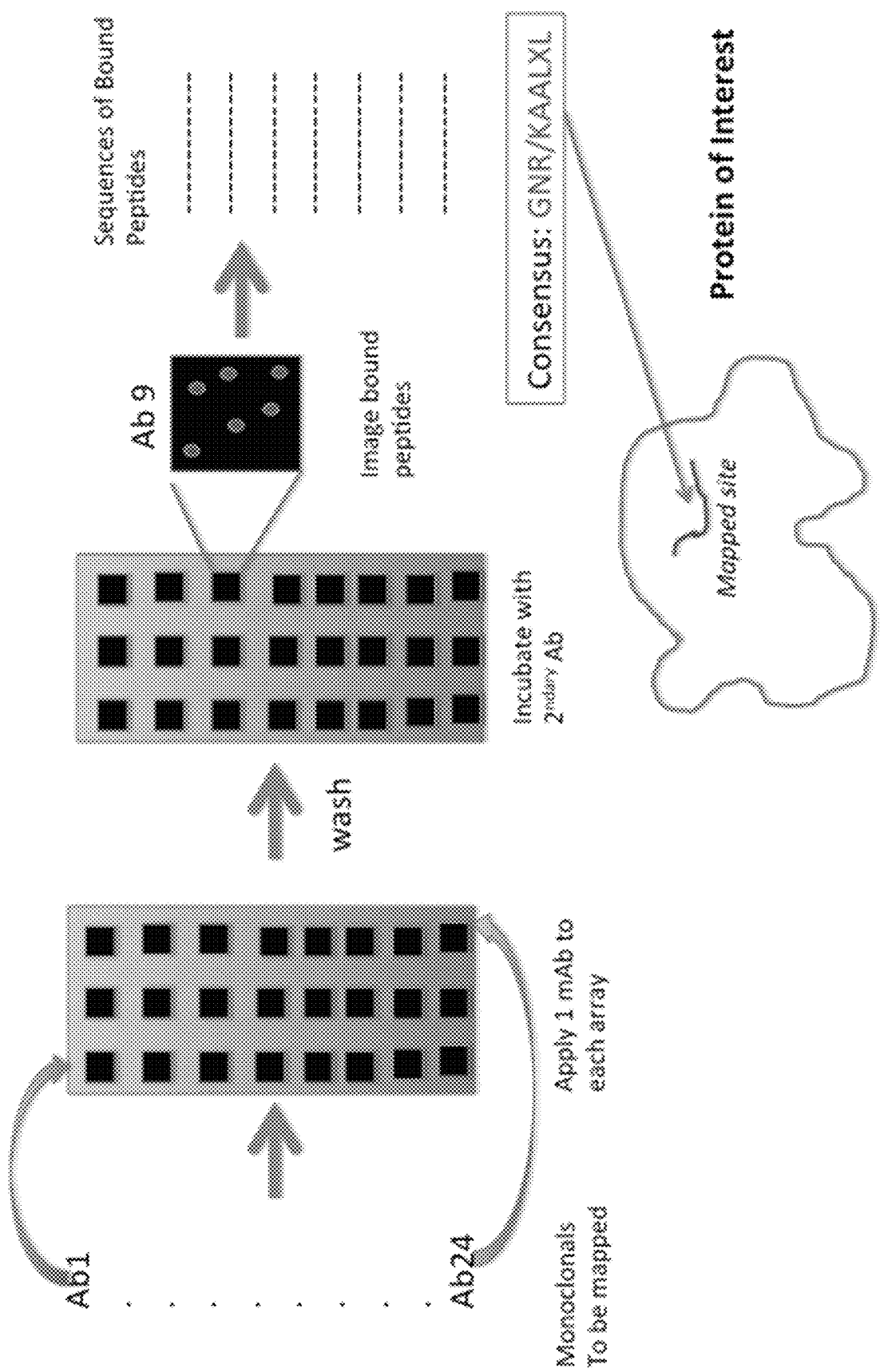
FIG. 1 is a schematic representation of a method of screening monoclonal antibodies as provided herein. A sample comprising a monoclonal antibody is applied to a random peptide library immobilized on an array, whereby the monoclonal antibody will bind to a subset of the peptides on the array. By aligning the sequence of the antibody-bound peptides, a consensus motif (SEQ ID NO: 268) can be determined.
Figure 2A:
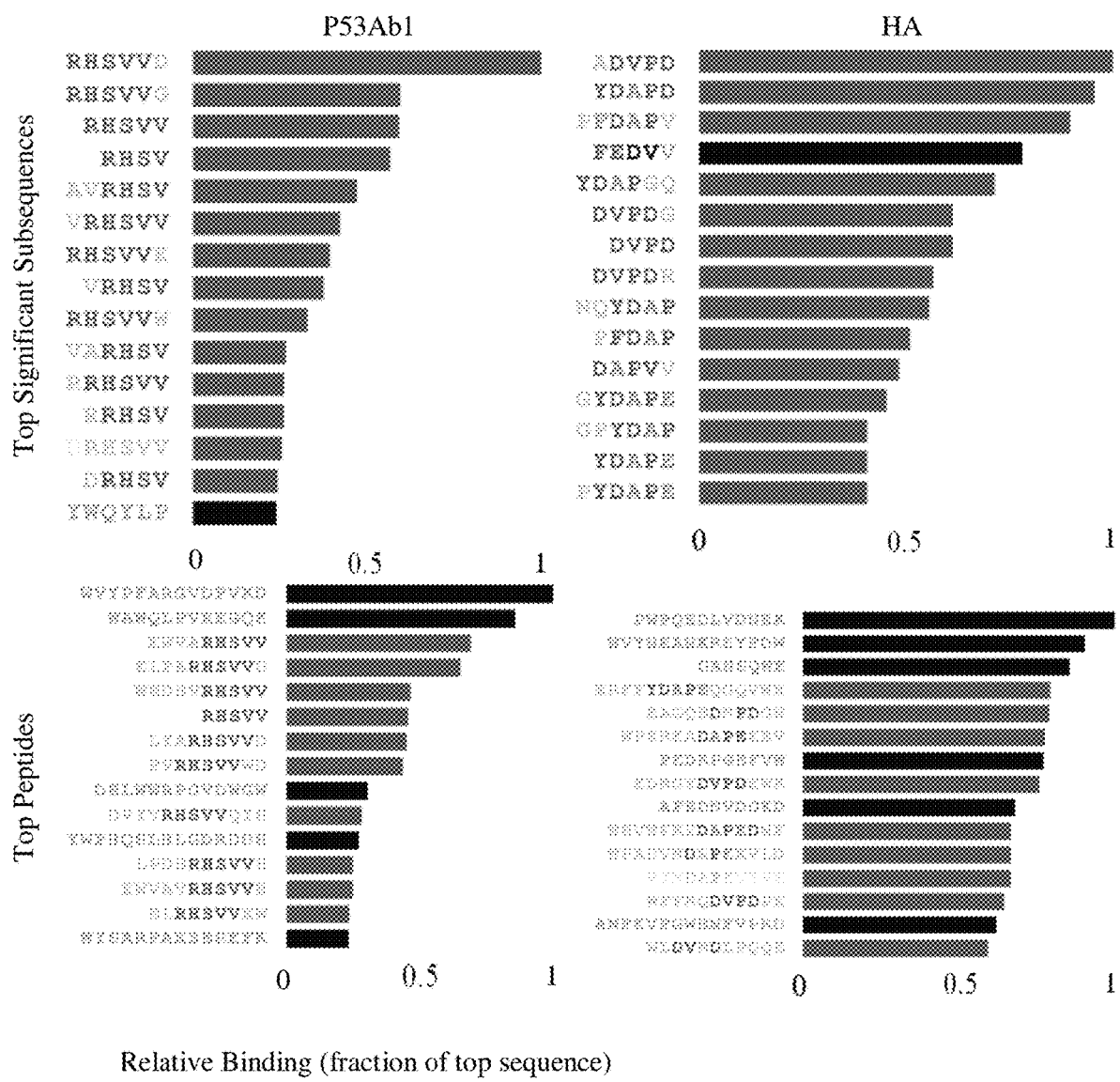
FIG. 2A illustrates top binding subsequences and peptides for the indicated monoclonal antibodies (SEQ ID NOS 1-60, top to bottom, left to right, respectively, in order of appearance). The upper panel shows the top binding subsequences, and the lower panel shows the subsequences for each monoclonal antibody tested.
Figure 2B:
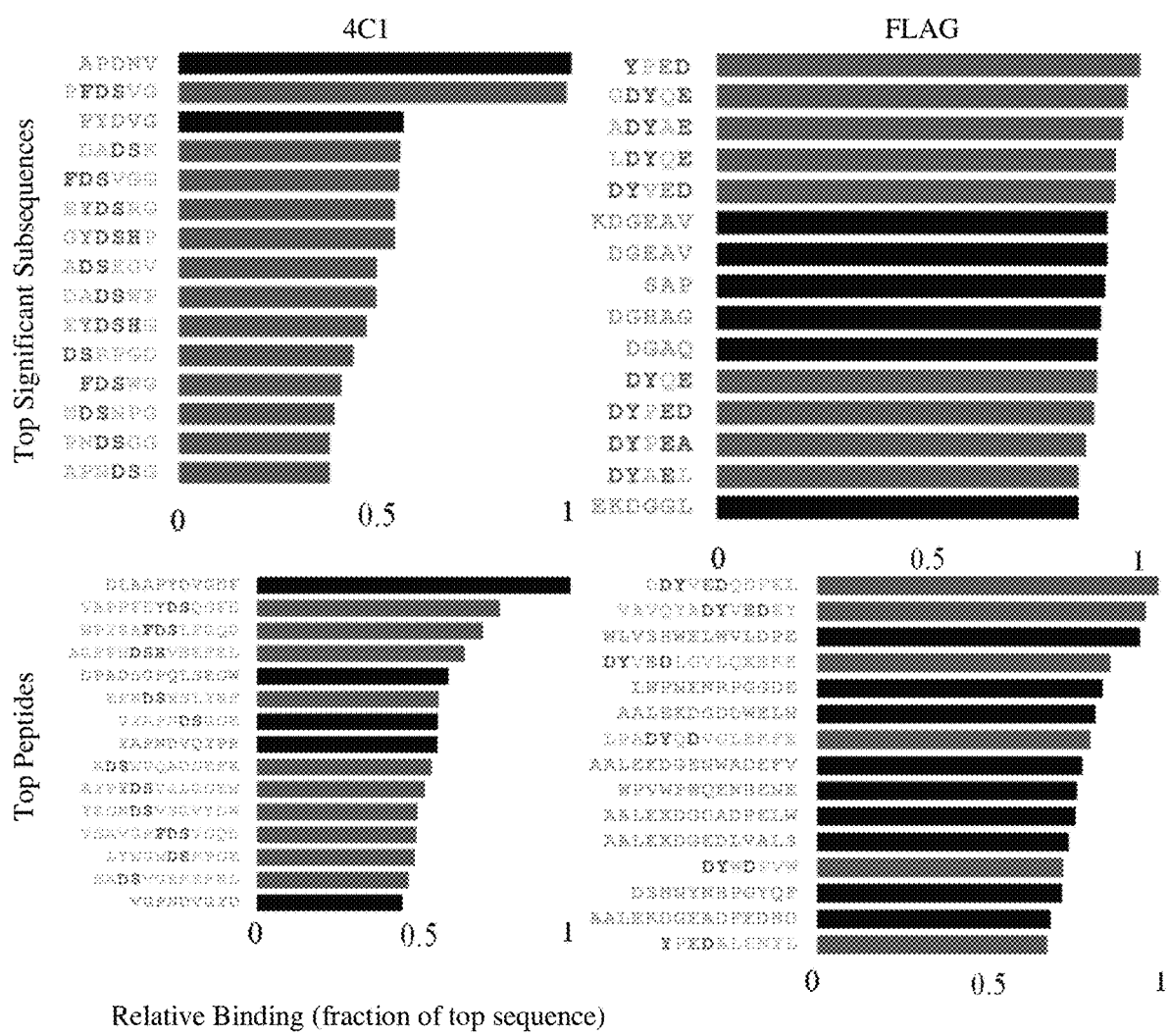
FIG. 2B illustrates top binding subsequences and peptides for the indicated monoclonal antibodies (SEQ ID NOS 61-120, top to bottom, left to right, respectively, in order of appearance). The upper panel shows the top binding subsequences, and the lower panel shows the subsequences for each monoclonal antibody tested.
Figure 2C:
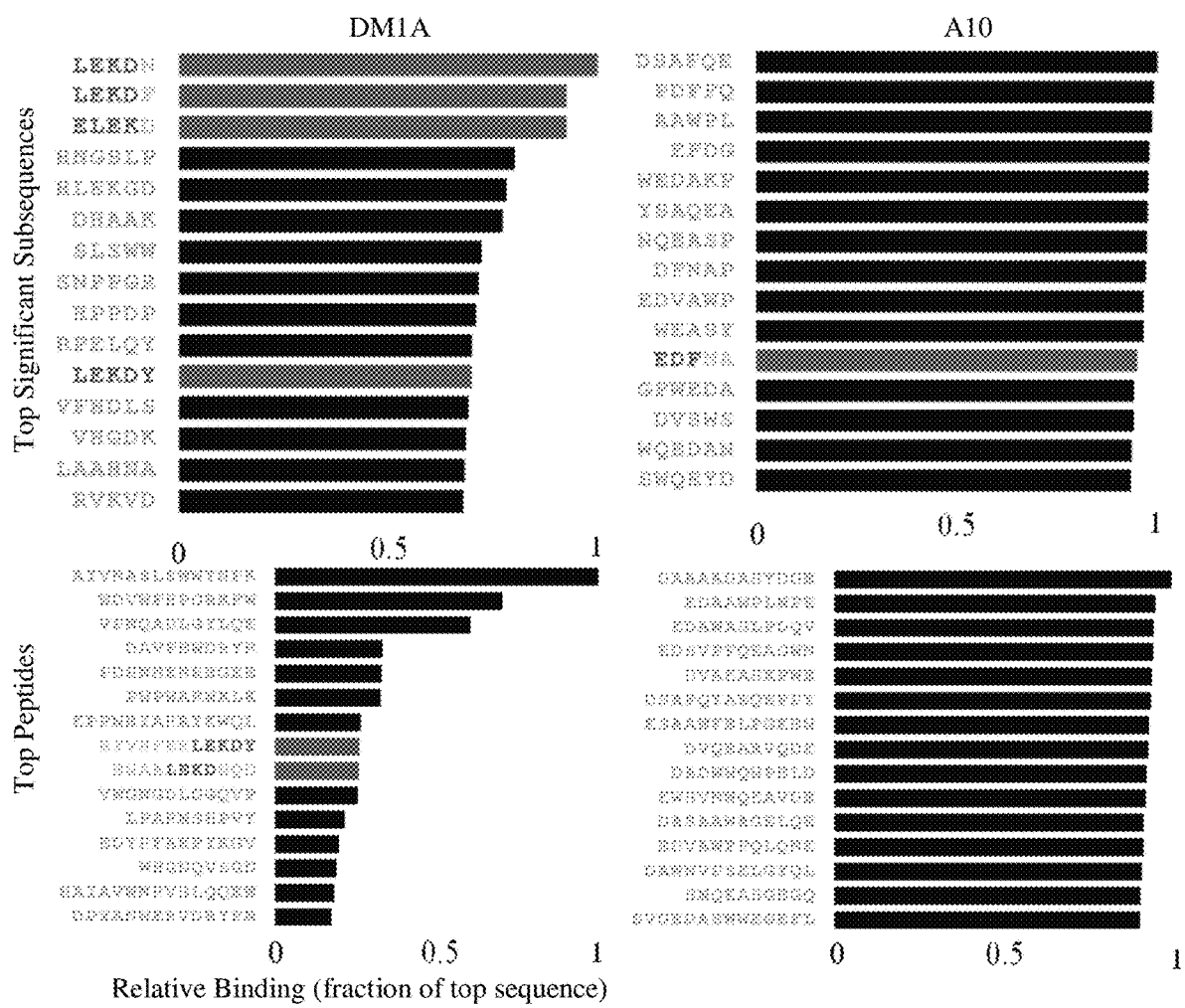
FIG. 2C illustrates top binding subsequences and peptides for the indicated monoclonal antibodies (SEQ ID NOS 121-180, top to bottom, left to right, respectively, in order of appearance). The upper panel shows the top binding subsequences, and the lower panel shows the subsequences for each monoclonal antibody tested.
Figure 2D:
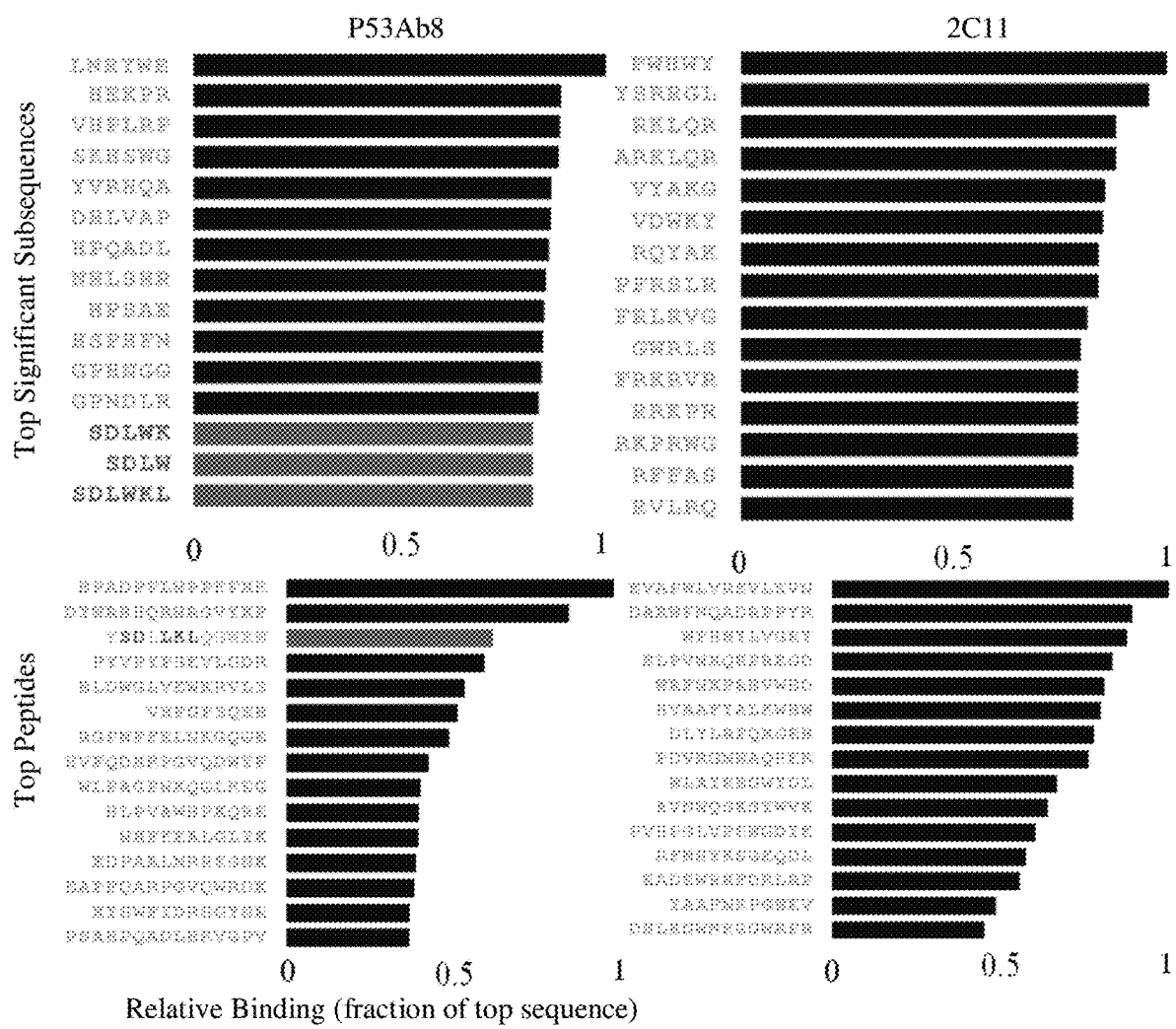
FIG. 2D illustrates top binding subsequences and peptides for the indicated monoclonal antibodies (SEQ ID NOS 181-240, top to bottom, left to right, respectively, in order of appearance). The upper panel shows the top binding subsequences, and the lower panel shows the subsequences for each monoclonal antibody tested.

Incorporated herein by reference in its entirety is Richer et al., *Molecular & Cellular Proteomics* 14.1:136-147, 2015.

Disclosed herein are devices, systems and processes for characterizing antibodies, including monoclonal antibodies, to regionally map the epitope to which the antibody binds. Standard methods for such antibody characterization, also known as epitope binning, typically involve surface plasmon resonance (SPR) technology. Using SPR, monoclonal antibody candidates are screened pairwise for binding to a target protein. Other standard methods involve ELISA-based screens but require synthesis of sets of overlapping peptides corresponding to each protein of interest. The systems and methods provided herein are based at least in part on the inventors' discovery that random peptide arrays can be employed for high-throughput monoclonal antibody profiling. Using random peptide arrays, it is possible to identify peptides that bind to proteins (or other macromolecules) for which peptide affinities were previously unknown. Moreover, the methods and systems provided herein make it possible to simultaneously screen numerous monoclonal antibodies for therapeutic drug development.

Methods

Provided herein are methods, systems and devices useful for screening a plurality of antibodies. By characterizing the binding sites of monoclonal antibodies (mAbs) on protein targets, the screening methods provided herein permit the high-throughput analysis and selection of the most suitable candidates for therapeutic monoclonal antibodies and antibody-based modalities.

In one aspect, the method comprises contacting a sample comprising a monoclonal antibody (mAb) to a plurality of random peptides immobilized on a support; identifying peptides recognized by the mAb; identifying amino acid sequences of mAb-bound peptides; and aligning said peptide sequences to identify one or more consensus motifs, where a consensus motif corresponds to an epitope to which the mAb binds. As used herein, the terms "antibody" and "immunoglobulin" refer to polyclonal and monoclonal antibodies, chimeric, and single chain antibodies, as well as the products of a Fab or other immunoglobulin expression library. The term "antibody" encompasses intact antibody molecules as well as antigen binding fragments thereof (including $F(ab')_2$, Fab, Fab', Fv, Fc, and Fd fragments). In some cases, the antibody is a chimeric antibody produced by recombinant methods to contain both the variable region of the antibody and an invariant or constant region of a human antibody. In other embodiments, the antibody is humanized by recombinant methods to combine the complementarity determining regions (CDRs) of the antibody with both the constant (C) regions and the framework regions from the variable (V) regions of a human antibody. Monoclonal antibodies, all derived from a single B-cell clone, exhibit specificity for a single epitope (also known as an antigenic determinant). As used herein, the term "monoclonal antibody" includes antibodies produced by an antibody-producing B cell that has been isolated and fused to an immortal hybridoma cell line in order to produce large quantities of identical monoclonal antibodies. Alternatively, monoclonal antibodies can be prepared using antibody engineering methods such as phage display. See, for example, U.S. Pat. Nos. 6,300,064 and 5,969,108; and "Antibody Engineering," McCafferty et al. (Eds.) (IRL Press 1996)).

As used herein, the terms "epitope" and "antigenic determinant" refer to a site on an antigen (e.g., target polypeptide) that is recognized by an immunoglobin or antigen and to which the immunoglobulin or antibody specifically binds. Epitopes can be linear or conformational. Generally, an epitope includes at least 3, 4, 5, 6, 7, 8, 9, 10, 11, 12, 13, 14, or 15 consecutive or non-consecutive amino acids in a unique spatial conformation. See, e.g., Epitope Mapping Protocols in Methods in Molecular Biology, Vol. 66, G. E. Morris, Ed. (1996). Encompassed by the term "epitope" are simple epitopes comprising only a few contiguous amino acid residues as well as complex epitopes that encompass discontinuous amino acids. In some cases, complex epitopes comprise amino acids separated in the primary sequence but in close proximity in the three-dimensional folded structure of an antigen. As used herein, the terms "specific binding," "selective binding," "selectively binds," and "specifically binds" refer to antibody binding to an epitope on a predetermined antigen. As used herein, the term "antibody affinity" refers to the strength of the interaction between an epitope and the antibody's antigen-binding site (also known as a paratrope). Generally, high affinity antibodies bind quickly and more tightly to the antigen and permit greater sensitivity in assays. In some cases, an antibody specifically or selectively binds with an affinity ($K_D$) of approximately less than $10^{-7}$ M, such as approximately less than $10^{-8}$ M, $10^{-9}$ M, or $10^{-10}$ M, or lower. The terms "$K_D$" and "$K_d$" are synonymous and refer to the dissociation equilibrium constant of a particular antibody-antigen interaction.

Specific binding can additionally or alternatively be defined as a binding strength (e.g., fluorescence intensity) more than three standard deviations greater than background represented by the mean binding strength of empty control areas in an array (i.e., having no compound, where any binding is nonspecific binding to the support). The range of affinities or avidities of compounds showing specific binding to a monoclonal or other sample can vary by from about 1 to about 4 and often from about 2.5 to about 3.5 orders of magnitude. Avidity is defined as enhanced binding of a component in solution to a surface that includes multiple copies of a compound, such as a peptide, that the solution component has affinity for. In other words, given a compound on a surface that individually has some affinity for a component of a solution, avidity reflects the enhanced apparent affinity that arises when multiple copies of the compound are present on the surface in close proximity. Avidity is distinct from cooperative binding in that the interaction does not involve simultaneous binding of a particular molecule from the solution to multiple molecules of the compound on the surface. Avidity interactions and/or cooperative binding can occur during the association of components of a solution, such as antibodies in blood, with compounds on a surface.

In exemplary embodiments, a sample comprising an antibody is contacted to a plurality of peptides immobilized on a support. The term "peptide" or "oligopeptide" as used herein refers to organic compounds composed of amino acids, which are arranged in a linear chain and joined together by peptide bonds between the carboxyl and amino groups of adjacent amino acid residues. The term "peptide" or "oligopeptide" preferably refers to organic compounds composed of less than 70 amino acid residues, more preferably of less than 35 amino acid residues, more preferably of less than 25 amino acid residues.

Preferably, the plurality of peptides comprises a random peptide library, meaning a library of randomly generated peptide sequences. A random peptide library comprises a plurality of randomly generated peptides without a priori assuming a set of eliciting proteins or proteome. In this manner, a random peptide library provides a universal, non-proteome-specific approach. In some cases, an immobilized random peptide library is a microarray. The term "microarray" as used herein refers to a two dimensional arrangement of features on the surface of a solid or semi-solid support. Features as used herein are defined areas on the microarray comprising biomolecules, such as peptides. The features can be designed in any shape, but preferably the features are designed as squares or rectangles. The features can exhibit any density of biomolecules. Preferably, a microarray comprises a high density of peptide features immobilized on a support. As the number of peptide features increases, the amount of information about the binding character of an antibody of interest increases. Arrays typically have at least 100 compounds. Arrays having between 500 and 500,000 compounds provide a compromise between likelihood of obtaining compounds with detectable binding to any target of interest and ease of synthesis and analysis. Arrays having, for example, 100 to 500,000 members or 500-500,000, or 1000-250,000 members can also be used. Arrays having, for example, between 10,000 and 100,000, between 25,000 and 500,000 or between 50,000 and 350,000 are also contemplated within the disclosures herein. In some cases, peptide density on an array is at least 10,000 peptide features per 1 cm$^2$. In other cases, peptide density on an array is at least 300,000 peptide features per 0.5 cm$^2$. The density of molecules on an array can be controlled by the attachment or in situ synthesis process by which a compound is attached to a support. The length of a coupling cycle and concentration of compound used in coupling can both affect compound density.

The spacing between compounds on an array also can be controlled. The density of different molecules of a compound within an area of an array or on a particle controls the average spacing between molecules of a compound (or compounds in the case of a pooled array), which in turn determines whether a compound is able to form enhanced apparent affinity to a sample (an avidity interaction). If two molecules of a compound or compounds in the case of a pooled array are sufficiently proximate to one another, both molecules can enhance apparent affinity to the same binding partner. In some arrays, at least 10%, 50%, 75%, 90% or 100% of compounds in the array are spaced so as to permit enhanced avidity interactions and/or undergo cooperative binding with a binding partner. However, it is not necessary that all compounds be deposited or synthesized with the same spacing of molecules within an area of the array. For example, in some arrays, some compounds are spaced further apart so as not to permit or permit only reduced avidity interactions or cooperative binding compared with other compounds in an array. Spacing peptides more than 3 nm or 4 nm apart is associated with higher affinity bindings. As spacing decreases (e.g., 1-2 nm) and density increases, lower affinity bindings are more prevalent. In exemplary embodiments, peptide spacing within a feature on the array is less than 3 nm, less than 2 nm or less than 1 nm. For peptides of length 15-25 residues an average (mean) spacing of less than 0.1-6 nm, 1-4 nm, 2-4 nm, e.g., 1, 2 or 3 nm is, for example, suitable to allow different regions of the same compound to undergo binding with enhanced apparent affinity. Average spacings are typically less than 6 nm because spacings of 6 nm or more do not allow avidity to enhance the apparent affinity for the target or cooperative binding to take place. For example, for peptides of lengths 15-25 residues, the two identical binding sites of one antibody could not span more than 6 nm to contact two peptides at once and bind cooperatively. The optimum spacing for enhancing avidity and/or cooperativity interactions may vary depending on the compounds used and the components of the sample being analyzed.

Peptide spacing on an array can be measured experimentally under given conditions of deposition by depositing fluorescently labeled compounds and counting photons emitted from an area of an array. The number of photons can be related to the number of molecules of fluorescein in such an area and in turn the number of molecules of compound bearing the label (see, e.g., U.S. Pat. No. 5,143,854). Alternatively, the spacing can be determined by calculation taking into account the number of molecules deposited within an area of an array, coupling efficiency and maximum density of functional groups, if any, to which compounds are being attached. The spacing can also be determined by electron microscopy of an array or via methods sensitive to the composition of molecules on a surface such as x-ray photoelectron spectroscopy or secondary ion mass spectrometry.

In exemplary embodiments, multiple peptides are immobilized in a pre-selected pattern on a solid support. The term "solid support" as used herein refers to any solid material, having a surface area to which organic molecules (e.g., peptides) can be attached through bond formation or absorbed through electronic or static interactions such as covalent bond or complex formation through a specific functional group. The solid support comprises any appropriate material such as, for example, glass, silicon, silica, polymeric material, poly(tetrafluoroethylene), poly(vinylidene difluoride), polystyrene, polycarbonate, polymethacrylate, ceramic material, and hydrophilic inorganic material. In some cases, the solid support comprises a hydrophilic inorganic material selected from the group consisting of at least one of alumina, zirconia, titania, and nickel oxide. In other cases, the support comprises a combination of materials such as plastic on glass, carbon on glass, and the like.

Preferably, a solution comprising an antibody of interest is contacted to a plurality of peptides immobilized on a support. As depicted in FIG. 1, the solution in some cases is a supernatant collected from a hybridoma culture. In exemplary embodiments, two or more samples comprising hybridoma supernatants generated from immunization with a target protein of interest are sampled individually on peptide arrays. Data collected from analysis of each array can be used to characterize each sample and to develop a molecular recognition or binding for the monoclonal antibody of each hybridoma supernatant.

Binding interactions between components of a sample (e.g., hybridoma supernatant) and an array can be detected in a variety of formats. In some formats, components of the samples are labeled. The label can be a radioisotope or dye among others. The label can be supplied either by administering the label to a patient before obtaining a sample or by linking the label to the sample or selective component(s) thereof.

In exemplary embodiments, detecting binding of an antibody to one or more peptides of the plurality is performed using any appropriate method including, without limitation, detection using a secondary detection reagent. In some cases, the secondary detection reagent is a fluorescently labeled secondary antibody. In other cases, monoclonal antibodies of the sample (e.g., a supernatant collected from a hybridoma culture) are directly labeled. Binding is then detected with a laser scanner. Alternatively, binding to the array can be directly detected using label-free methods such as surface plasmon resonance (SPR) and mass spectrometry. SPR can provide a measure of dissociation constants and dissociation rates.

Optionally, binding interactions between component(s) of a sample and the array can be detected in a competition format. A difference in the binding profile of an array to a sample in the presence versus absence of a competitive inhibitor of binding can be useful in characterizing the sample. The competitive inhibitor can be for example, a known protein associated with a disease condition, such as pathogen or antibody to a pathogen. A reduction in binding of member(s) of the array to a sample in the presence of such a competitor provides an indication that the pathogen is present. Stringency can be adjusted by varying the salts, ionic strength, organic solvent content and temperature at which library members are contacted with the target.

In exemplary embodiments, the amino acid sequence of each peptide of the plurality on the array is known. In such cases, the amino acid sequences of the peptides to which binding is detected are aligned and compared for shared or consensus amino acid motifs. Such sequence alignments can be performed by any appropriate sequence comparison method. For example, the sequences of peptides binding the antibody can be aligned to the protein antigen sequence using a sequence alignment program that performs extensive computations of user data. For example, BLAST software can be used. In such cases, a given sequence entered by a user is aligned and compared against all sequences in a database containing, for example, all proteins, all proteins with structures, all antibody proteins with structures, or all human antibody proteins with structures. In some cases, antigenic peptide sequences are compared against databases including, without limitation, Swiss-PROT, NBRF/PIR, PRF, and GENPEPT using, for example, Fasta or Smith-Waterman algorithms. Examples of existing databases describing the expressed proteins of various organisms include: UniProt (Universal Protein Resource; uniprot.org on the World Wide Web); Ensembl (ensembl.org on the World Wide Web); VEGA (Vertebrate Genome Annotation; vega.sanger.ac.uk/ on the World Wide Web); CCDS (Consensus CDS; ncbi.nlm.nih.gov/projects/CCDS/ on the World Wide Web); UCSC Genome Browser (genome.ucsc.edu on the World Wide Web); Protein database at NCBI (ncbi.nlm.nih.gov/protein on the World Wide Web); and RCSB Protein Data Bank (pdb.org/on the World Wide Web).

Through sequence alignment, it is possible to identify epitope(s) recognized by the antibody of interest. By examining related sequences on the array that are not bound, the essential amino acids for binding can be defined. By examining the number and diversity of non-binding epitope sites, the promiscuity of the antibody can be quantified.

As used herein, the term "motif" refers to a pattern of residues in an amino acid sequence or nucleotide sequence of a defined length that is conserved or shared among two or more sequences. Consensus motifs identified according to a method provided herein are advantageously contiguous motifs of the genetic sequence and represent a linear sequence of the gene. In some cases, however, motifs identified according to a method provided herein is noncontiguous on the linear sequence of the gene. Deterministic motif finding algorithms useful for the methods provided herein include TEIRESIAS (Rigoutsos and Floratos, *Bioinformatics* 14:55-67 (1998)) and PRATT (Jonassen, *Comput. Appl. Biosci.* 13:509-522 (1997)).

The methods provided herein permit simultaneous detection of multiple high and low-affinity epitopes of multiple monoclonal antibodies. In exemplary embodiments, the methods also identify monoclonal antibodies reactive to and specific for highly conserved epitopes. The ability to detect low-affinity interactions is particularly advantageous for characterizing candidate therapeutic monoclonal antibodies. While therapeutic antibodies often exhibit high affinity toward their antigen, low affinity off-target binding can affect pharmokinetics of a therapeutic mAb.

Array Construction

Peptide microarrays were manufactured using in situ synthesis of 330,000 random-sequence peptides per each 1-cm$^2$ region. Each 75 mm×25 mm slide contained 24 subarrays, each containing the 330,000 peptides. The average length of each peptide was 11.2 amino acids with a standard deviation of ±1.3, normally distributed. The longest peptide was 22 amino acids long, and the shortest was 1 amino acid, with 95% of peptides between 8 amino acids and 14 amino acids. Peptides were synthesized from the C terminus to the N terminus, with the amine group farthest from the array surface.

Prior to assay, arrays were washed in 100% N,N-dimethylformamide for one hour and then introduced to an incubation buffer consisting of 3% BSA in PBS with 0.05% Tween 20 over a period of six hours to allow the solvent phase to completely transition to the aqueous phase. The arrays were then processed via incubation in the presence of antibodies or serum and detected by fluorescent antibody (Legutki J. B. et al., Nat. Commun. 5:4785 (2014)).

Binding Antibodies to the Array

Residual N,N-dimethylformamide was removed by two 5-min washes in distilled water. Arrays were equilibrated in PBS for 30 min and blocked in the incubation buffer. Arrays were washed and briefly spun dry prior to being loaded into the 24-well gasket (Array-It, Santa Clara, Calif.). Incubation buffer was added to each well (100 µl), and 100 µl of 1:2500 diluted sera was added for a final concentration of 1:5000. Arrays were incubated for 1 h at 23° C. with rocking and then washed with incubation buffer plus 1% BSA using a BioTek 405TS plate washer (Biotek, Winooski, Vt.). Anti-human IgG-DyLight 549 (KPL, Gaithersburg, Md.) was added to a final concentration of 5.0 nm to detect the human primary IgG. Unbound secondary antibody was then removed by washing in incubation buffer followed by washing in distilled water (5 min each). The arrays were removed from the gasket while submerged, dunked in isopropanol, and centrifuged dry (800×g, 5 min). Arrays were scanned at 533 nm using an Innoscan 910 array scanner (Innopsys, Carbonne, France). Features were aligned and extracted using GenePix Pro 6.0 (Molecular Devices, Sunnyvale, Calif.).

Monoclonal Antibodies

Eight monoclonal antibodies were used in this study: anti-human HA (Rockland Antibodies, Rockland, Md., [YPYDVPDYA] (SEQ ID NO: 241)), DM1A (anti-human tubulin, Invitrogen/Invitrogen, [AALEKDYEEVGV] (SEQ ID NO: 242)), Ab1 (anti-human TP53 antibodies, Clontech, Palo Alto, Calif., [TFRHSVVV] (SEQ ID NO: 243)), FLAG (Invitrogen, Madison, Wis., [DYKDDDDK] (SEQ ID NO: 244)), 4C1 (anti-human TSHR, Santa Cruz Biotechnology, Dallas, Tex., [QAFDSHY] (SEQ ID NO: 245)), A10 (Acris Antibodies GmbH, Hiddenhausen, Germany, [EEDFRV] (SEQ ID NO: 246)), Ab8 (Anti-human P53, Thermo Fisher Scientific, Waltham, Mass., [TFSDLWKLLPE] (SEQ ID NO: 247)), and 2C11 (Acris Antibodies GmbH, [NAHYYVFFEEQE] (SEQ ID NO: 248)).

Serum Samples

Sera from seven different disease cohorts and 10 pools of healthy persons (designated as Human Normal Pool) were provided by Seracare Life Sciences (Milford, Mass.). An additional control group of 32 different non-infected volunteers was collected from consenting individuals by the Center for Innovations in Medicine at Arizona State University under IRB #0905004024 (renewed April 2014). The eight cohorts used in this study included 32 healthy (Normals), 9 dengue fever (DEN1 Flaviviridae), 8 Lyme disease (*Borrelia burgdorferi*), 7 syphilis (*Treponema palladium*), 13 malaria (*Plasmodium falciparum*), 12 whooping cough (*Bordetella pertussis*), 15 hepatitis B virus (Hepadnavirus), and 10 mixed pools of normal subjects (Healthy Normal Pool).

Analytical Methods

Finding Antibody-Specific Peptides

The goal of this study was to find sequence motifs corresponding to an epitope. The first step was to identify peptides that bind specifically to the sample of interest without regard to the peptide sequence. First, arrays were normalized to the median intensity value to account for small differences in serum or dye concentrations. Then, the fold-change was calculated per peptide across the sample of interest (numerator) versus the median of control samples (denominator). The controls for the serum study comprised the 32 healthy volunteers referred to as Normals. The controls for the monoclonal antibody study were a mix of all monoclonal antibodies in this study. For each test, the top 500 peptides were used as seed sequences for epitope discovery.

Maximal Subsequence Algorithm

The algorithm used to find high binding subsequences was designed to find short consensus motifs within a large set of random peptides. It can be divided into two parts: motif identification and significance testing. Seed sequences are computationally divided into all possible subsequences within a certain range of lengths (three to seven amino acids). The sets of these subsequences $S_x$ are ranked and evaluated for significance in subsequent steps. The input to the algorithm is a set of sequences $S=\{s_1, s_2, \ldots, s_n\}$ and associated preprocessed array intensity values $Q=\{q_1, q_2, \ldots, q_n\}$. To find a set of significant subsequences, the sequences in S are divided into all possible subsequences containing between three and seven amino acids each. For example, the sequence AVHAD (SEQ ID NO: 249) would be divided into the set {AVH, VHA, HAD, AVHA (SEQ ID NO: 250), VHAD (SEQ ID NO: 251), AVHAD SEQ ID NO: 249)}.

All the subsequences in S constitute a new set, S'. Members in S' have one or more associated values in Q corresponding to the intensities from parent sequences containing that subsequence. The function $Q_{sub}$ as $S' \rightarrow Q^m$ is defined where m is the number of peptides excepting the top 500 seed peptides containing the input subsequence. This gives all intensity values associated with a subsequence.

Sequences $s_i \in S_x$ are ranked according to their associated values $t_i = Q_{sub}(s_i)$. A subsequence is considered only if it appears in at least three peptides ($t_i > 3$). This value is the support of the subsequence. The ranking function considers the support and the median intensity value median($t_i$), such that the highest ranked subsequences have at least three appearances on the array and have high median intensities. This criterion is not strictly necessary, but it simplifies significance testing by throwing out non-significant, poorly represented sequences. Once subsequences are filtered and ranked, their significance can be established. This occurs for a given subsequence i using the following nonparametric procedure:

1. Draw $t_i$ values from Q at random. Call this vector $t'_i$.
2. Compute median($t'_i$).
3. Repeat steps one and two 10,000 times, resulting in a nonparametric estimate of a $t_i$ null distribution. Call this vector D.
4. A p value is computed for subsequence $s_i$ according to $p_i = [\Sigma_{k \in D} I(\text{median}(t'_i) > k)]/|D|$, where I is the indicator function.
5. Correct the p values for multiple hypotheses. The following correction function was used: $p'_i = p_i/[\Sigma_{s_i \in S x}|Q_{sub}(s_i)|]$. For example, if 1000 subsequences are considered, α is 1/1000, resulting in one expected false positive.

Calling Epitope Candidates

Figure 5A:
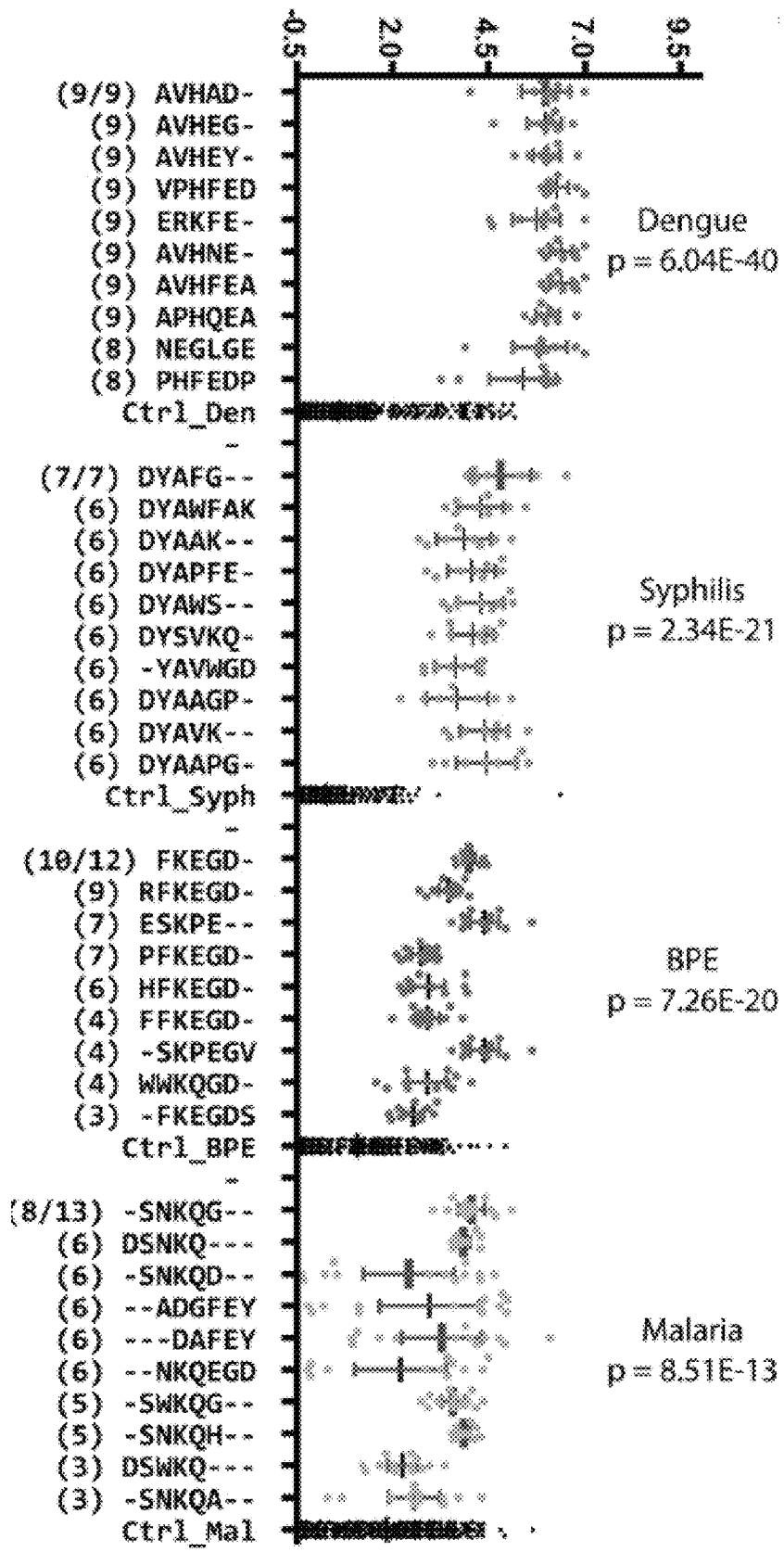
FIG. 5A illustrates the top significant subsequences for disease cohorts. Panels show the top 10 most commonly appearing and significant subsequences in serum samples from the indicated disease cohorts (SEQ ID NOS 324-362, respectively, in order of appearance).
Figure 5B:
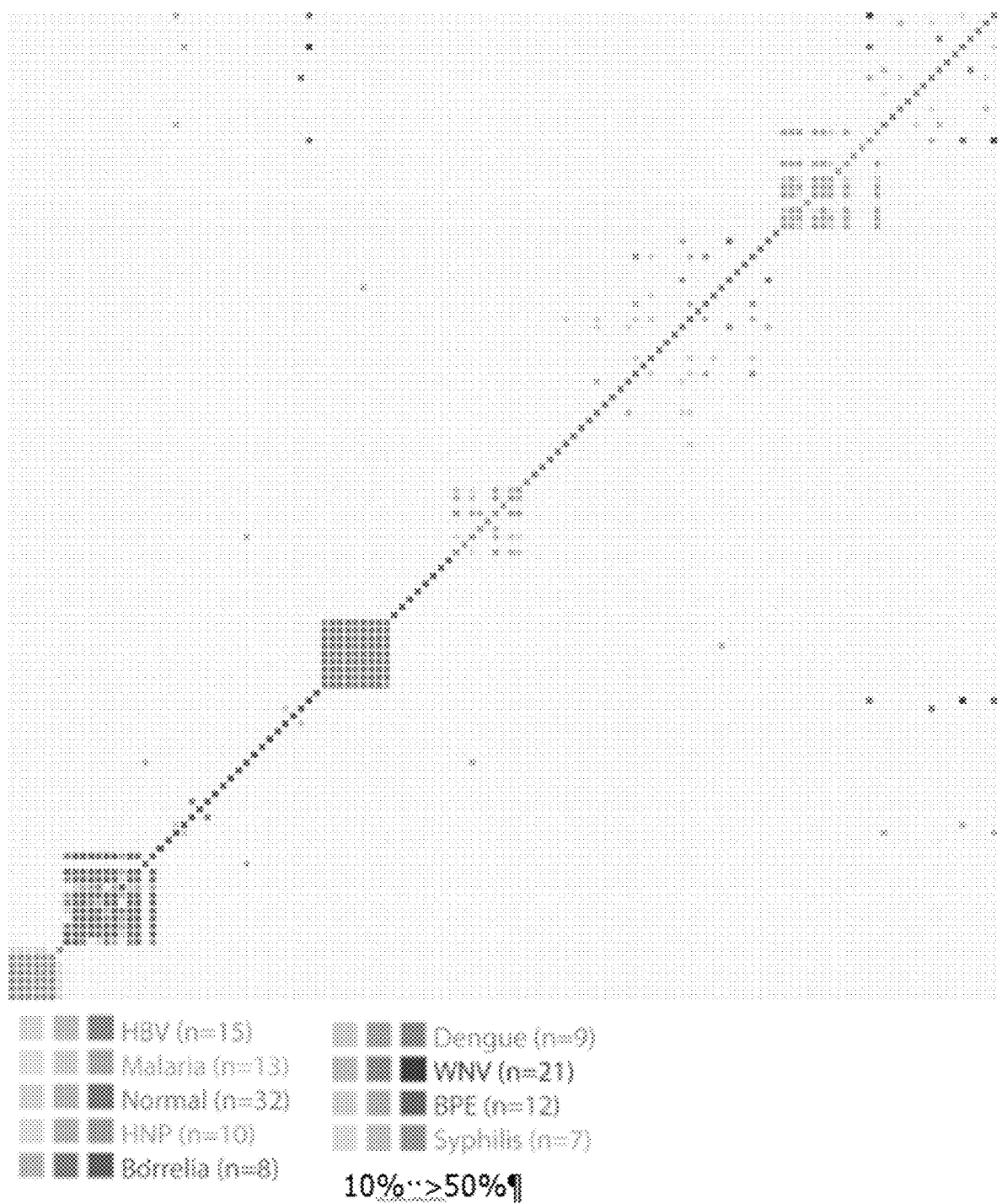
FIG. 5B illustrates the top significant subsequences for disease cohorts. The pairwise fractional overlap in significant subsequences is shown. BPE, *Bordetella pertussis*; HNP, Human Normal Pools, a collection of pools of non-disease individuals.

Significant subsequences were identified for each individual per disease cohort. In order to determine the most likely epitope candidates, the sequences were ranked in terms of the number of subjects in which they were called significant. The sequences that appeared most often in different individuals within the same group were deemed the most likely epitope candidates (FIGS. 5A-B).

Mapping Epitope Candidates to Pathogen Proteomes

The most common significant subsequences (query sequences) were searched against the pathogen proteome for 100% identity. The probability of a match was assessed by searching randomly drawn array sequences of the same length as the query sequence against the proteome and comparing the expected number of matches to those observed with the query.

Pathogen Identification

The objective was to identify an unknown pathogen based on array sequence information alone. The n significant subsequences from the same cohort were pairwise aligned using the BLOSUM62 substitution matrix, producing an (n×n) matrix of alignment scores. This matrix was hierarchically clustered by single linkage, producing a dendrogram of related subsequences. This analysis revealed peaks of central subsequences that were presumed to be most closely related to the true epitope. These peak sequences were searched against a database of 596 proteomes (hereinafter called the Pathogen Proteome Database) from various strains of pathogenic bacteria, viruses, and protists causing over 100 different diseases. Those proteins and organisms matching all queried sequences with 100% or 80% identity were noted. Probabilities were determined by querying the database with randomly drawn sequences as above.

Minimum Required Sequence Information

In order to find the point at which pathogen proteins could be resolved from a database given fixed epitope information, several sets of random sequences were generated ranging in length from four to seven amino acids. Pairs of sequences with set lengths were drawn from this set and queried against two databases: one containing 596 human pathogens, and another containing over 5000 bacteria, viral, and eukaryotic proteomes. These two databases helped establish the point at which pathogens could be uniquely resolved. For example, any given trimer sequence would be present in many pathogen proteins, but two heptamer sequences are unlikely to appear in a given pathogen protein by chance.

Sequence Logo Generation

Significant subsequences were collected together into a FASTA-formatted list. Multiple alignments were produced with ClustalW2 (Chaddock A. M., et al., EMBO J. 14, 2715

(1995)). A multiple-alignment text file was used as input to WebLogo3 (Bähler M., Rhoads A, FEBS Lett. 513, 107-113 (2002)) using default settings, producing the motif figure.

E-value Calculations

The reported E-values were calculated by searching random re-orderings (with replacement) of the candidate subsequence against the target proteome, using the mean number of occurrences of 10,000 re-orderings as the E-value.

The following examples are presented by way of illustration and not limitation.

Example 1

Epitope Determination in Monoclonal Antibodies

Experiments were designed to determine whether one could predicatively map epitopes to well-characterized monoclonal antibodies. Eight antibodies with reactivity to a known linear sequence were chosen and analyzed.

Table 1 lists peptides and binding intensities for the eight different monoclonal antibodies. Monoclonal antibodies were used to test the motif search analysis algorithm. The highest rated subsequences were related to the true epitope and to each other to an extent that ensured the emergence of a conserved motif with strong association to the epitope sequence. Ab, antibody; GRAVY, grand average of hydropathicity index (Legutki J. B., Nat. Commun. 5:4785, (2014)).

The bar plots in FIGS. 2A-D show the top binding subsequences (top panel) and subsequences (bottom panel) for each of the eight tested monoclonal antibodies. P53Ab1 (RHSVV (SEQ ID NO: 254)), HA (DVPD (SEQ ID NO: 256)), 4C1 (FDSH (SEQ ID NO: 257)), and FLAG (DYDDDK (SEQ ID NO: 258)) each had on-target motifs that were identified within each of the top binding peptides, and these were enhanced through subsequence analysis (shown in red). DM1A (ALEKD (SEQ ID NO: 259)) had few on-target motifs in its top peptides, but subsequence analysis revealed the true epitope. FLAG cross-reacted most strongly with the epitope from DM1A (ALEKDY (SEQ ID NO: 260)), but subsequence analysis successfully removed this effect.

Table 2 shows the number of peptides for each antibody that yielded a signal greater than 5-fold above background ("total binders") and how many of those had at least 80% sequence identity with the true epitope ("on target"). See Table 1 for a list of true epitopes. A very low percentage (<11%) of the binding peptides had strong sequence similarity with the true epitope, in agreement with previous studies (Halperin R. F. et al., Mol. Cell. Proteomics 10, 10(3):M110.000786 (2011)).

TABLE 1

Monoclonal antibodies used in this study

| Epitope | SEQ ID NO: | Ab name | Immunogen | Isotype | pI | GRAVY | Mean signal intensity | Mapped predicatively |
|---|---|---|---|---|---|---|---|---|
| EEDFRV | 246 | A10 | Human Pol II | IgG2b | 4.1 | −1.3 | 4911 | No |
| SDLWKL | 252 | p53ab8 | Human p53 | IgG2b, IgG2a | 5.6 | −0.3 | 6243 | No |
| QAFDSH | 253 | 4C1 | Human insulin receptor | IgG2a | 5.1 | −1.1 | 971 | Yes |
| RHSVV | 254 | p53ab1 | Human p53 | IgG1 | 9.8 | 0 | 5074 | Yes |
| DYKDDDDK | 244 | FLAG | FLAG peptide | IgG1 | 4 | −3.3 | 1167 | Yes |
| AALEKD | 255 | DM1A | Human tubulin α | IgG1κ | 4.7 | −0.6 | 5798 | Yes |
| YPYDVPDYA | 241 | HA | HA peptide | IgG1 | 3.6 | −0.9 | 905 | Yes |
| NAHYYVFFEE-QE | 248 | 2C11 | Human insulin receptor | IgG1 | 4.5 | −1 | 827 | No |

The linear epitope for each monoclonal antibody was known and was used as the basis for algorithm development and testing as indicated above. In most cases, simply sorting peptides by intensity per monoclonal antibody was insufficient to reveal epitope motifs among the highest binding peptides. Variation in binding to a specific target comes in part from the amount of non-cognate binding. Highly promiscuous antibodies such as anti-HA bind large numbers of peptides with low similarity to the target, and this created a lack of specificity in the datasets (FIGS. 2A-D, Table 2).

TABLE 2

On-target versus off-target binding

| | Total binders | On target | Fraction |
|---|---|---|---|
| AB1 | 42,386 | 466 | $1.10 \times 10^{-2}$ |
| HA | 1608 | 53 | $3.30 \times 10^{-2}$ |
| 4C1 | 2561 | 276 | $1.08 \times 10^{-1}$ |
| FLAG | 7563 | 0 | 0 |
| DM1A | 44,821 | 207 | $4.62 \times 10^{-3}$ |
| A10 | 44,924 | 37 | $8.24 \times 10^{-4}$ |

TABLE 2-continued

On-target versus off-target binding

| | Total binders | On target | Fraction |
|---|---|---|---|
| AB8 | 46,327 | 1 | $2.16 \times 10^{-5}$ |
| 2C11 | 671 | 0 | 0 |

Thus, transforming the data in terms of peptide subsequences revealed highly specific and consistent motifs that corresponded to epitope targets in five of the tested antibodies. Motifs were similar to the exact eliciting peptide sequence. Even when the exact sequence was not present on the array, sequences very similar to the eliciting peptide predominated (FIGS. 2A-D and FIGS. 3A-B).

Figure 3A:
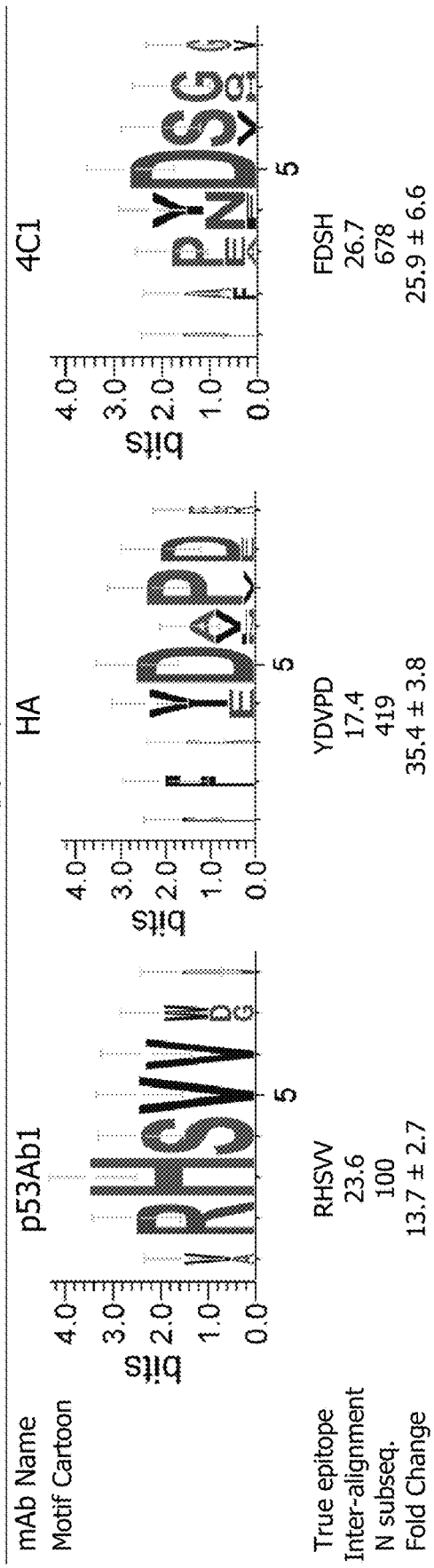
FIG. 3A illustrates monoclonal antibody motifs and their corresponding epitopes (SEQ ID NOS 254, 269, 257, 270 and 271, respectively, in order of appearance). Panels show the motifs for the indicated monoclonal antibodies after incubation on peptide microarrays and subsequence analysis.
Figure 3A:
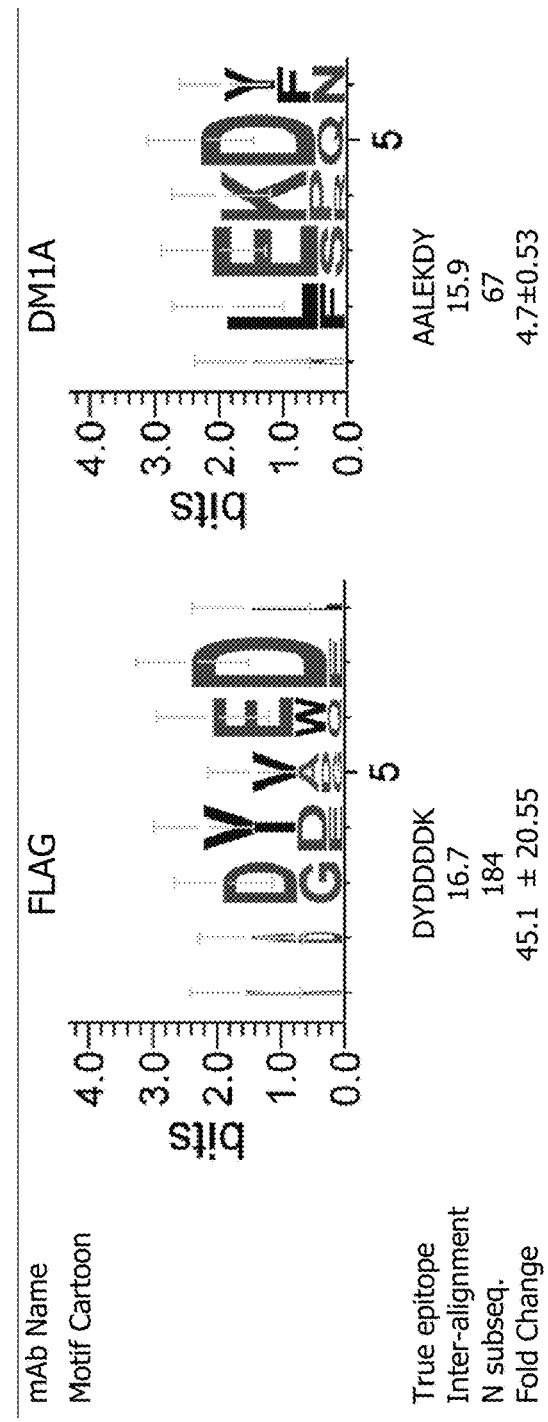

FIG. 3A shows the five motifs that were revealed after monoclonal antibodies were incubated on the peptide microarrays and subsequence analysis was performed. Sequence logos were created using the top 10 most highly ranked subsequences obtained from the peptide sequences. Weblogos suggested positional dependence with dominating anchor residues and linking or non-anchor regions. "True epitope" is the sequence determined by the manufacturer. "Inter-alignment" is the expected value of pairwise gapless alignment scores (BLOSUM62 matrix) between any two significant subsequences pulled from the arrays. "Fold change" indicates the relative binding strength of the peptides making up the motif versus the median binding intensity for that peptide in the other monoclonal antibodies tested. Antibodies for which consensus motifs could not be found were A10 (EEDFRV (SEQ ID NO: 246)), p53Ab8 (SDLWKL (SEQ ID NO: 252)), and 2C11 (NAHYYVFFE-EQE (SEQ ID NO: 248)). Additional information about these antibodies and their immunogens can be found in Table 1.

Figure 3B:
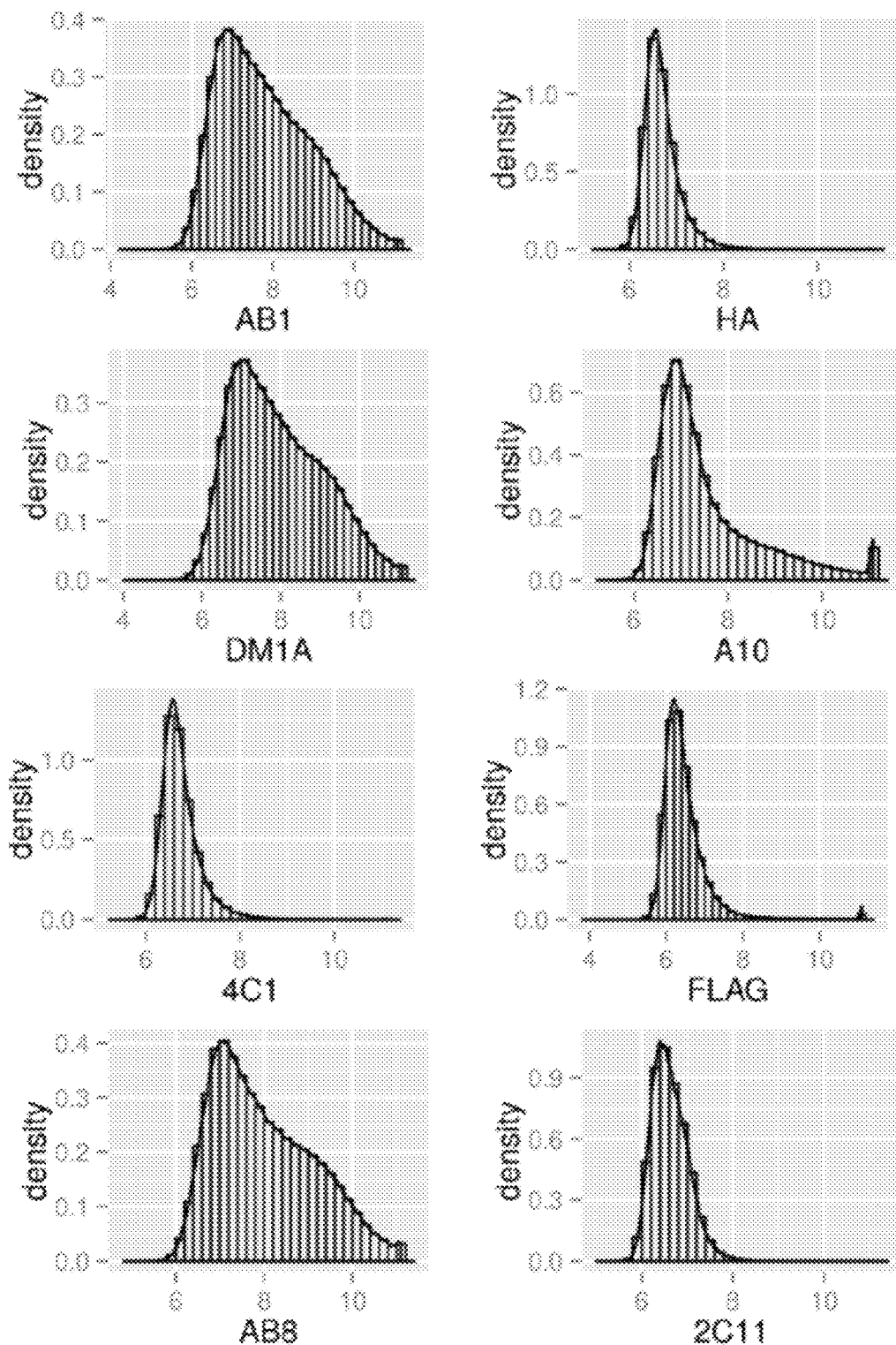
FIG. 3B illustrates monoclonal antibody motifs and their corresponding epitopes. Panels show histograms of binding profiles for each monoclonal antibody tested.

FIG. 3B shows histograms of each monoclonal antibody tested. The x-axis is the log 10 normalized signal intensity, and the y-axis is the data density. Antibodies demonstrated varied binding profiles, with monoclonals such as HA, 4C1, and FLAG showing a narrow distribution around low intensities, and others such as AB1 and DM1A demonstrating a broader binding profile. See Table 2 for an analysis of on-target versus off-target binding.

As stated above, three of the tested antibodies did not generate a specific response to the expected target sequence. In one of these cases (P53Ab8), the epitope SDLWKL (SEQ ID NO: 252) was bound, but because of the high degree of cross-reactivity to non-sequence-similar peptides, one would not expect to map the epitope based on these results alone (FIG. 4A).

FIG. 4A shows the top 25 sequence motifs found for monoclonal antibodies HA (left) and p53 (right). Red outlined regions indicate the closest match to the actual epitope for the given monoclonal antibody. The black number is the average fold change of the peptides containing the indicated motif relative to the same peptides for all other monoclonal antibodies. Although small differences occurred, there is a consensus pattern. In contrast, p53Ab1 (right) demonstrated high overall binding to the true epitope but cross-reacted with many other sequence clusters, preventing good prediction and yielding low fold-change values.

Figure 4B:
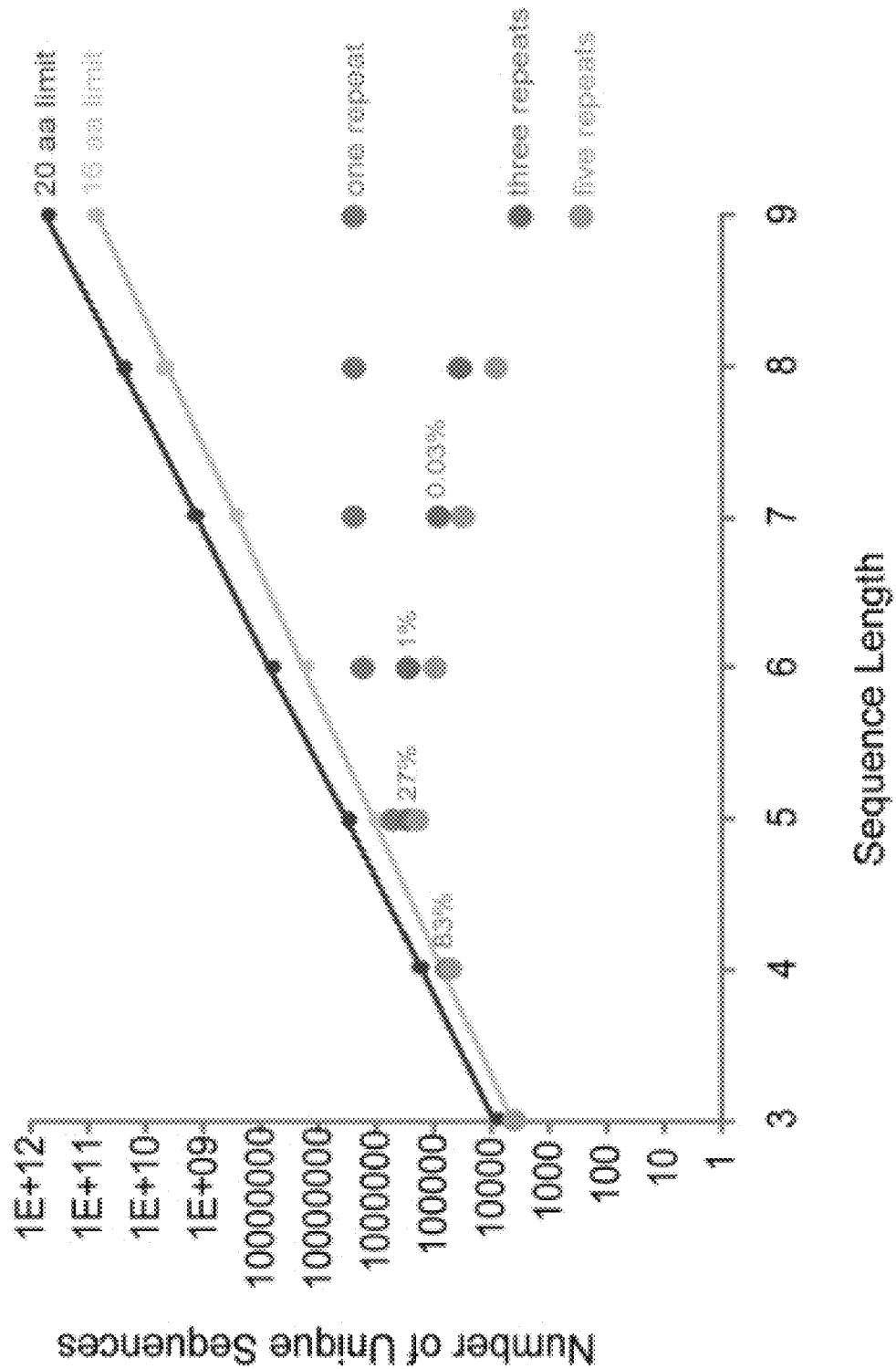
FIG. 4B illustrates sequence representation and predictive versus non-predictive subsequences. The fraction of all possible k-mers present on the array as a function of κ-mer length is shown.

FIG. 4B shows the fraction of all possible k-mers present on the array as a function of k-mer length. The arrays represent 27% of all possible 5-mers redundantly.

Example 2

Groupwise Epitope Determination in Patient Sera

Eight cohorts representing seven different diseases and one group of healthy volunteers were tested using the described methods.

FIG. 5A shows the top 10 most commonly appearing and significant subsequences in serum samples from the indicated disease cohorts. The number of patients within that cohort for which that sequence was called significant is shown in parentheses to the left. The y-axis is categorical and shows each subsequence; the x-axis is the maximum log 10-normalized intensity of the peptide binding on the array for each patient. The total number of samples in each cohort is given as a fraction at the top. Subsequences with exact matches to proteins within the pathogen are indicated with vertical red bars. The top ranked sequences are listed in Table 3 that shows discovered epitope sequences and their proposed antigen mappings as described below (Example 3).

TABLE 3

Proposed epitope mappings for disease cohorts

| Sequence | SEQ ID NO: | Infection | Organism | Antigen | Known Antigen | In IEDB | Membrane Protein | Putative or Hypothetical | E Value | P Value |
|---|---|---|---|---|---|---|---|---|---|---|
| AVHAD | 249 | Dengue | Dengue virus (1-3) | NS1 | Yes | Yes | N/A | No | 0.0005 | 0.0004 |
| REGEK | 261 | Dengue | Dengue virus 4 | Serine protease NS3 | Yes | Yes | N/A | No | 0.00083 | 0.0007 |
| DYAFG | 262 | Syphylis | Treponema pallidum | Lipoprotein | No | No | Yes | Yes | 0.27 | 0.26 |
| EDAK | 263 | Lyme's Disease | Borrelia burgdorferi | OspF | Yes | No | Yes | No | 4.6 | 0.98 |
| FKEG | 264 | Pertussis | Bordetella pertussis | Multi-drug Resistance protein | No | No | Yes | Yes | 3.5 | 0.96 |

TABLE 3 -continued

Proposed epitope mappings for disease cohorts

| Sequence | SEQ ID NO: | Infection | Organism | Antigen | Known Antigen | In IEDB | Membrane Protein | Putative or Hypothetical | E Value | P Value |
|---|---|---|---|---|---|---|---|---|---|---|
| SNKQG, RLKEP | 265, 266 | Malaria | Plasmodium falciparum | RESA-like protein | Yes | No | Yes | No | 0.072 | 0.067 |
| DAFEY | 267 | Malaria | Plasmodium falciparum | pfEMP1 | Yes | No | Yes | No | 3.5 | 0.96 |

Several of the cohorts performed similarly to the monoclonal antibodies in that they identified a relatively small number of peptides with highly homogeneous sequence motifs that were obvious and visible by simple text matching. These cohorts produced a noticeably homogeneous list of peptide sequences that deviated little from a single and readily apparent motif. The multiple alignments of the top 10 sequences for each of these disease cohorts are shown in FIG. 5B. Of the seven disease cohorts tested, five revealed a clear consensus sequence.

FIG. 5B shows the pairwise fractional overlap in significant subsequences. A colored, saturated cell represents a pair of patients in the same cohort that shared at least 50% of their significant subsequences. Grayscale cells represent pairs of patients from different cohorts whose immune systems see similar sequences. Individuals within the same disease cohort showed much more overlap between their significant subsequences than those in different cohorts or the normal cohort, indicating an association between the discovered sequences and the disease state.

Example 3

Identification of Consensus Sequences in Pathogen Proteomes

In order to test whether the groupwise consensus motifs (FIGS. 4A-B) corresponded with true epitopes, the Immune Epitope Database was searched for exact substring matches to sequences from these lists. Despite the small size of this database, the sequence AVHAD (SEQ ID NO: 249) from dengue was present in the database and indicated as an epitope from the NS1 protein in two dengue strains (E-value: $5 \times 10^{-4}$).

Further analysis of the other cohorts revealed additional matches to antigenic proteins. The sequence EDAK (SEQ ID NO: 263) from Borrelia mapped to known antigen OspF (E-value: 4.6), and DYAFG (SEQ ID NO: 262) from syphilis mapped to a lipoprotein in several strains of T. pallidum (E-value: 0.27). Malaria contained sequences SNKQG (SEQ ID NO: 265) and RLKEP (SEQ ID NO: 266) (FIG. 7), both of which mapped to the ring-infect erythrocyte surface antigen (RESA) protein in P. falciparum 3D7 (E-value: 0.072), and another sequence (DAFEY (SEQ ID NO: 267)) mapping to one of the pfEMP1 variants in P. falciparum (E-value: 3.5). The sequence FKEG (SEQ ID NO: 264) mapped to an MDR efflux protein in B. pertussis (E-value: 3.5). These results are summarized in Table 3 above.

The two dengue epitopes shown in Table 3 were previously verified using peptide tiling of the NS1 and NS3 proteins against dengue sera. Another two (EDAK (SEQ ID NO: 263), DAFEY (SEQ ID NO: 267)) map to known and characterized antigens in Borrelia burgdorferi and Plasmodium falciparum, respectively. The remainder displayed motif conservation consistent with epitopes but mapped to hypothetical proteins. "E-value" refers to the expected number of matches to the presumed epitope sequence(s) within the proteome of interest; "p value" refers to the chance of encountering at least one instance of the sequence within the proteome of interest. Not all proposed epitopes mapped to the proteome with significant p values, but they are reported here as a "best guess" to explain the high response to these sequences on the arrays.

These sequences were short as a result of platform limitations, and the E-values for these matches varied based on the size of the proteome. The dengue sequences are unlikely to arise by chance, at least given the size of the initial peptide library, with E-values $<10^{-3}$. Likewise, the two matches to the RESA protein in P. falciparum together had a low E-value of 0.072 corresponding to a p value of 0.067 (see Table 4).

TABLE 4

Sensitivity and specificity of epitope candidates

| Sequence | SEQ ID NO: | Infection | Sensitivity | Specificity |
|---|---|---|---|---|
| AVHAD | 249 | Dengue | 1 | 1 |
| REGEK | 261 | Dengue | N/A | N/A |
| DYAFG | 262 | Syphilis | 1 | 1 |
| EDAK | 263 | Lyme disease | 0.125 | 1 |
| FKEG | 264 | Pertussis | 0.83 | 1 |
| SNKQG, RLKEP | 265, 266 | Malaria | 0.69 | 1 |
| DAFEY | 267 | Malaria | 0.46 | 1 |

The selection algorithm maximizes sensitivity and might not be a reliable estimate of performance. However, the candidates shown in Table 4 do map to antigenic proteins and are specific to the cohort of interest. Estimates for the REGEK sequence (SEQ ID NO: 261) from dengue could not be computed, as this was discovered using a separate set of arrays or too few samples were processed.

Example 4

Individual Epitope Determination in Patient Sera

In order to test the heterogeneity within disease groups, the question was asked whether subsequences were differentially bound between individuals in disease cohorts and normal subjects. It was found that epitope sequences revealed in the groupwise analysis were present in most of the individuals from that group. All nine dengue samples contained AVHAD (SEQ ID NO: 249) as a significant subsequence. To visualize the extent of this overlap, the pairwise overlap of significant subsequences was calculated between individuals across disease groups (FIG. 5B).

FIG. 5B shows the pairwise fractional overlap in significant subsequences. A colored, saturated cell represents a pair of patients in the same cohort that shared at least 50% of their significant subsequences. Grayscale cells represent pairs of patients from different cohorts whose immune systems see similar sequences. Individuals within the same disease cohort showed much more overlap between their significant subsequences than those in different cohorts or the normal cohort, indicating an association between the discovered sequences and the disease state.

The feature selection process for the seed peptides requires that antibodies be commonly expressed within a disease cohort. Thus, the antibodies analyzed here displayed highly similar sequences across all individuals within a cohort. These sequences were equally unlikely to appear in other disease groups, also because of the feature selection requirements. However, it should be noted that peptides (features) common within a cohort demonstrated qualitatively greater fold-changes relative to Normals than those with less common sequences within a cohort.

Example 5

Additional Library Complexity Reveals Additonal Epitopes

This assay relies on many simultaneous measurements of antibody/peptide interactions. It is useful to know how changes in library content affect results. As only 27% of pentamers were represented on the original arrays, it was hypothesized that a different random library would result in additional targets that were invisible to the original experiments because they were not present. To test this, another array was created with a different set of 330,000 sequences. An attempt was made to find epitopes using a dengue-infected serum sample. This analysis revealed an additional epitope (REGEK (SEQ ID NO: 261), Dengue 4, E-value: $8.3 \times 10^{-4}$) that was previously mapped in the Immune Epitope Database but not present on the original array (FIG. 6).

Figure 6:
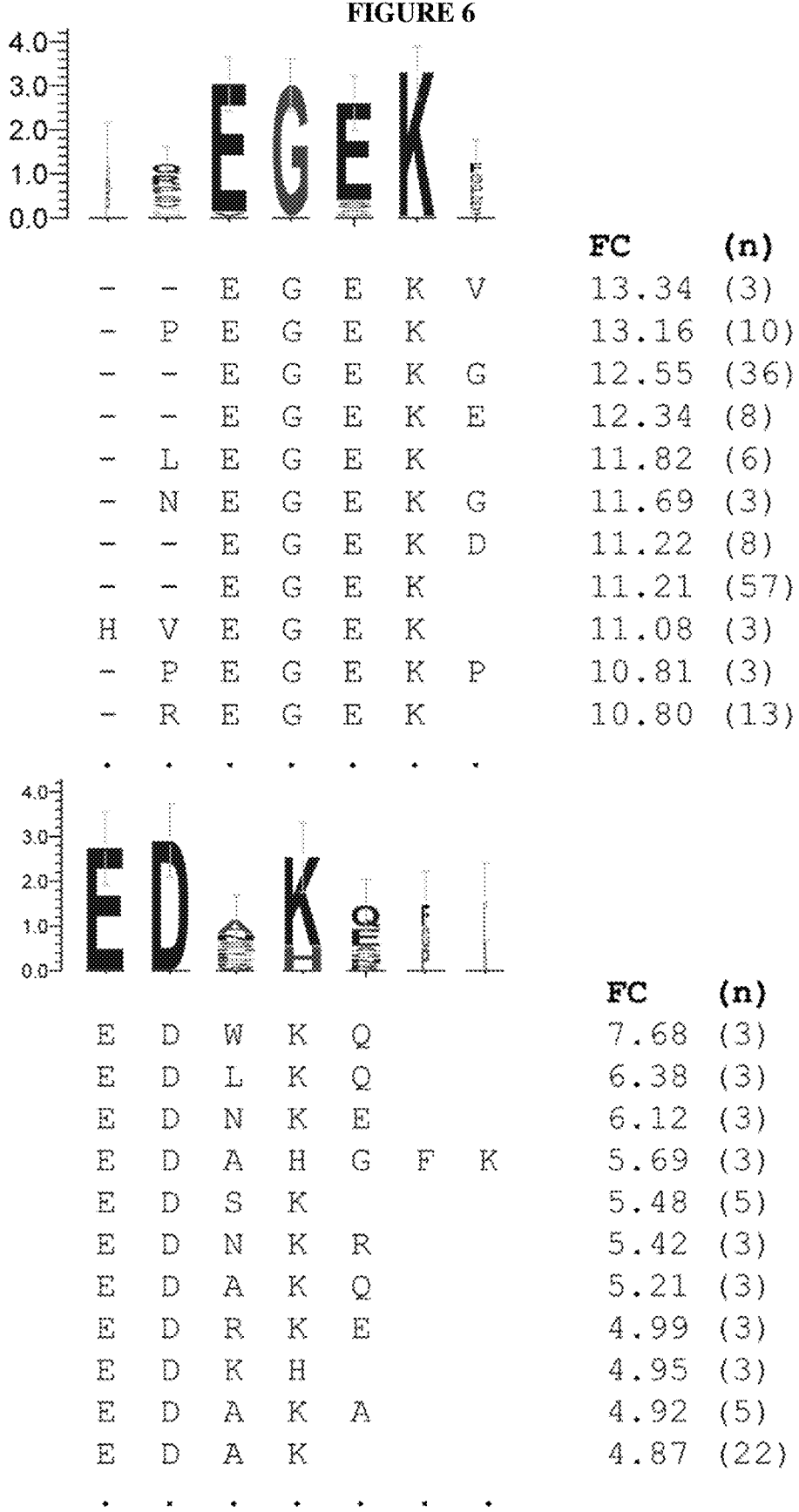
FIG. 6 illustrates motifs found in single patients (SEQ ID NOS 363-384, respectively, in order of appearance). The left panel shows a motif found in a single dengue patient that maps to NS3. The right panel shows a motif present in a single *Borrelia* patient that maps to the OspF protein. FC, fold change between the individual serum sample and a cohort of normal samples; n, number of peptides associated with that subsequence.

The motifs shown in FIG. 6 were associated with single patients within a disease cohort. The motif on the left was found in a single dengue patient and maps to NS3 (Garcia G. V. D., Del Angel R. M., Am. J. Trop. Med. Hyg. 56, 466-470 (1997)). It is a mapped epitope and was observable on the random-sequence peptide microarrays. The motif on the right was present in a single *Borrelia* patient and maps to the OspF protein, known to be associated with an immune response in dogs (Wagner B. et al., Clin. Vaccine Immunol. 19, 527-535 (2012)).

This result suggests that larger arrays should reveal additional antibodies. This experiment did not address specificity, however, and might not be the final argument supporting larger peptide libraries. In order to properly address that question, the second 330,000-peptide library would have to be added to the first and 660,000 peptides would have to be exposed to the sera simultaneously.

Example 6

Mapping Epitope Information to a Database

Having demonstrated that peptide microarrays are capable of resolving epitopes, experiments were designed to determine whether these sequences could predict the eliciting protein from a database of pathogen protein sequences.

Resolving a pathogen in a database given a few short sequences depends on both the size of the database and the length of the consensus motif. It was predicted that when one is using pairs of randomly generated sequences of varying lengths, a pair of pentamers, if known exactly, or a pair of heptamers, if known within 80% identity, is sufficient for resolving a pathogen in the Pathogen Proteome Database (FIG. 7).

Figure 7:
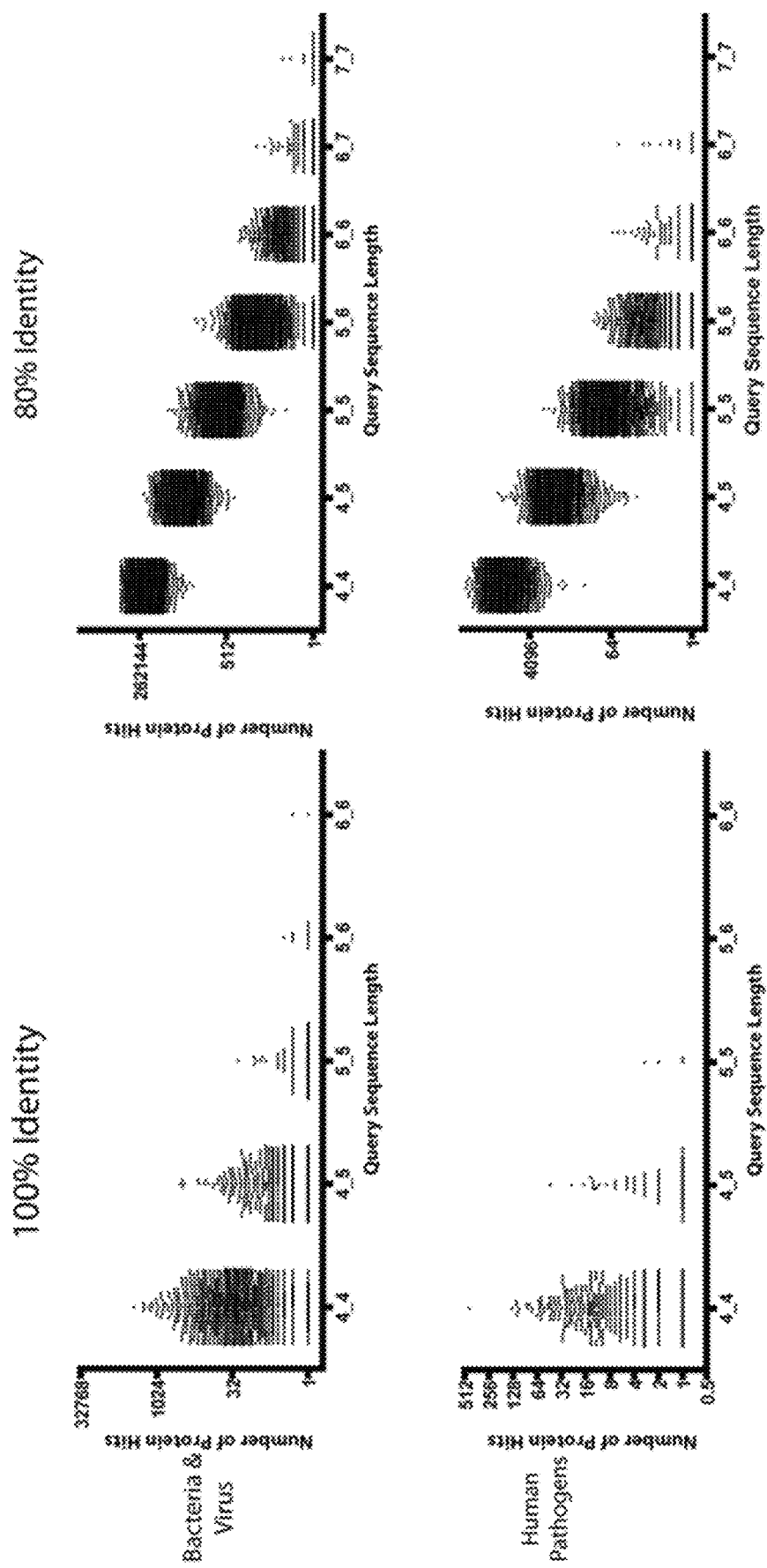
FIG. 7 illustrates finding arbitrary pathogen sequences in a pathogen database. Plots show the distribution of hits to pairs of arbitrary sequences of fixed lengths.

As shown in FIG. 7, pairs of k-mers with specified lengths were drawn at random from the distribution associated with array sequences. These were searched against two databases, one containing over 4000 bacteria and viruses (top), and another containing 596 human pathogens (bottom). The plots suggest that when two 7-mer linear epitopes from the same protein antigen are known with at least 80% identity, unique pathogen identification is reliably predicted.

Example 7

Deciphering Eliciting Pathogen Proteins

Figure 8A:
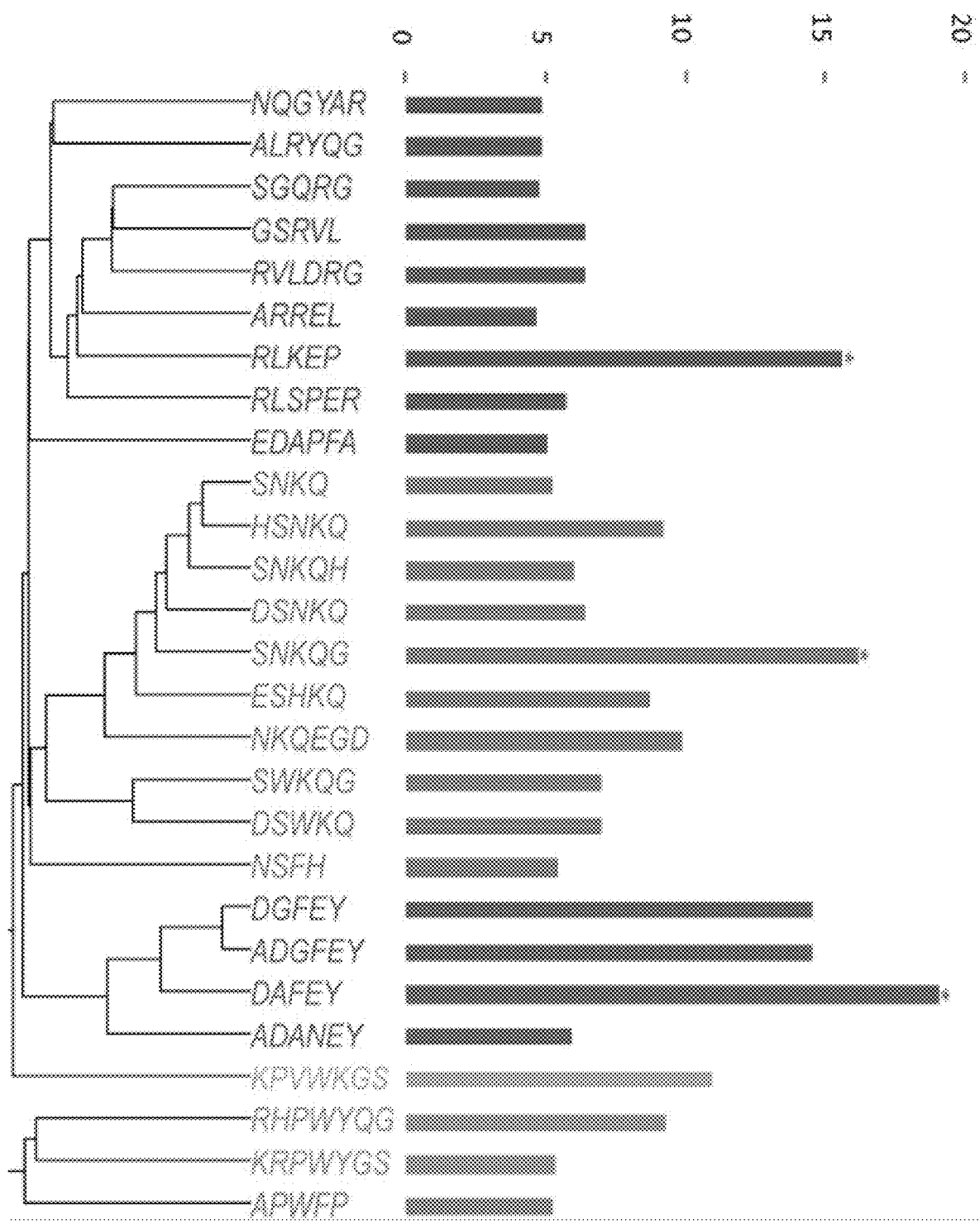
FIG. 8A illustrates using significant subsequences to identify an eliciting pathogen. Sample specific significant subsequences from the malaria cohort are shown (SEQ ID NOS 385-411, respectively, in order of appearance).
Figure 8B:
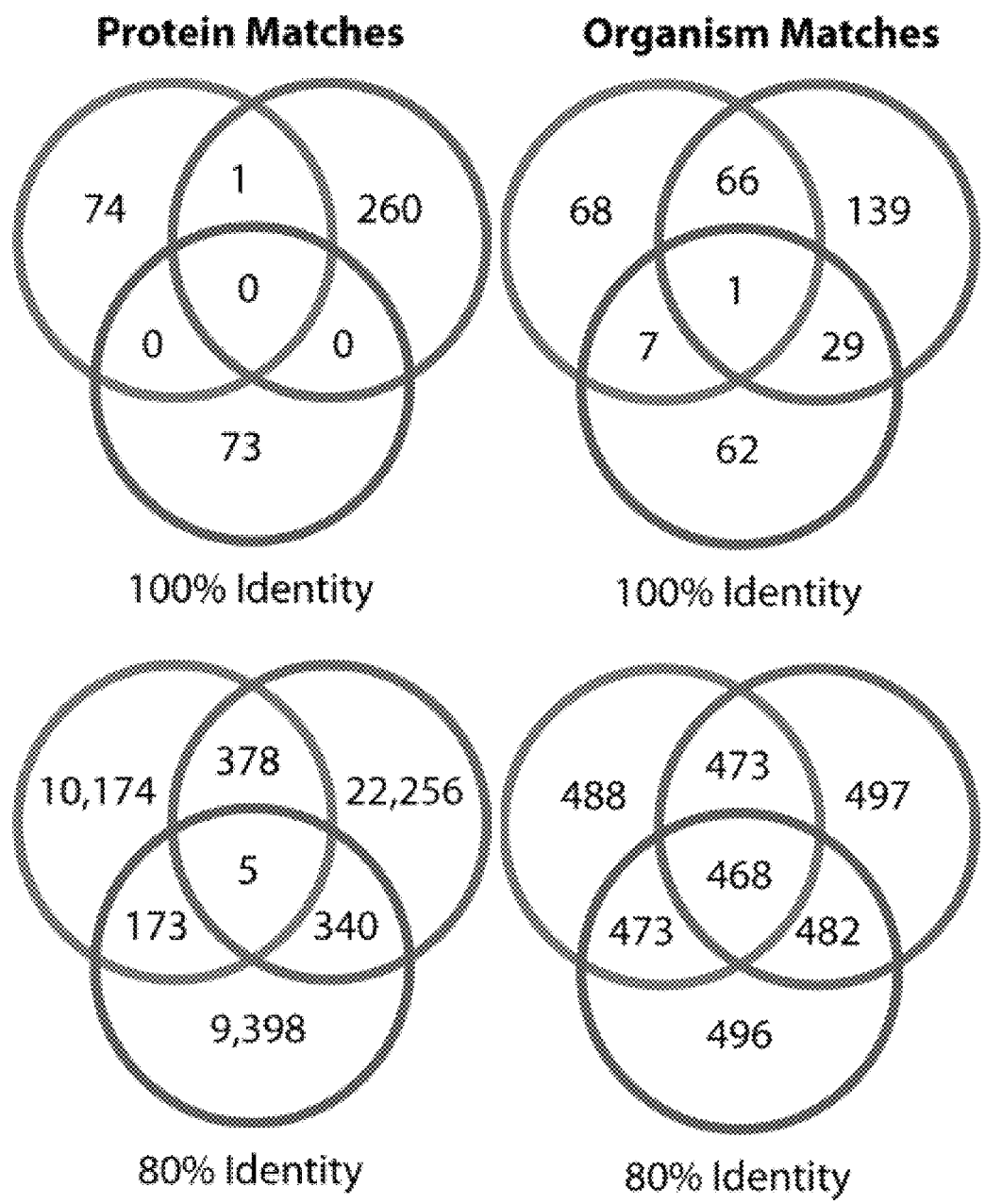
FIG. 8B illustrates using significant subsequences to identify an eliciting pathogen. Protein matches and organism matches from the malaria cohort are shown.

To improve sensitivity, it was opted for a restrictive search, relying on exact or near-exact (80%) identity and matches in the same protein to multiple pentamer queries. Using significant subsequences from malaria subjects, three epitope candidates (SNKQG (SEQ ID NO: 265), RLKEP (SEQ ID NO: 266), SNKQG (SEQ ID NO: 265)) were found. Searching these candidates against the Pathogen Proteome Database (multiple strains of each pathogen) resulted in uniquely identified membrane proteins from *P. falciparum* matching all three query sequences with 80% identity (FIGS. 8A-B). Two of the query sequences matched with 100% identity to a RESA-like protein, a known antigen in *Plasmodium* infections. The probability of two randomly drawn pentamers matching to one or more proteins globally in this database of over 1 million sequences is <0.01.

As shown in FIGS. 8A-B, sample specific significant subsequences from the malaria cohort were combined, aligned, and hierarchically clustered by single linkage. This revealed three distinct epitope candidates, indicated by red asterisks. These three sequences were queried against a database of 596 human pathogens for exact and 80% identity. Only one protein from *P. falciparum* out of all human pathogens contained both RLKEP SEQ ID NO: 266) and SNKQG (SEQ ID NO: 265). The probability of two array 5-mers hitting the same protein by chance is <0.001.

Although the embodiments are described in considerable detail with reference to certain methods and materials, one skilled in the art will appreciate that the disclosure herein can be practiced by other than the described embodiments, which have been presented for purposes of illustration and not of limitation. Therefore, the scope of the appended claims should not be limited to the description of the embodiments contained herein.

We claim:

1. A method of identifying an epitope recognized by an antibody, the method comprising the steps of:
   (a) contacting a sample comprising the antibody to a plurality of peptides immobilized on an array, wherein the array comprises at least 10,000 peptide features per 1 cm$^2$, wherein the peptides are spaced no more than 3 nm apart, wherein 95% of the peptides are in a range of 8 amino acids and 14 amino acids, and wherein the peptides are selected without a priori assuming a set of eliciting proteins or proteome;
   (b) identifying peptides that bind to the antibody with a K$_d$ of less than 10$^{-7}$ M; and
   (c) screening peptide sequences of the identified peptides for a consensus sequence motif, wherein the motif corresponds to an epitope of an antigen to which the antibody specifically binds.

2. The method of claim 1, wherein screening the peptide sequences of the identified peptides for a consensus sequence motif comprises using a search algorithm.

3. The method of claim 1, wherein identifying peptides that bind to the antibody comprises an immunofluorescence assay.

4. The method of claim 1, wherein screening the peptide sequences of the identified peptides for a consensus sequence motif comprises aligning the peptide sequences using a search algorithm.

5. The method of claim 1, wherein the antibody is a monoclonal antibody.

6. The method of claim 1, wherein the sample comprises an antibody that recognizes an epitope in an antigen from an infectious organism.

7. The method of claim 1, further comprising identifying a protein target of the antibody, comprising:
   (i) searching a protein sequence database for proteins that contain sequences homologous to the consensus sequence motif;
   (ii) identifying proteins from step (i); and
   (iii) verifying that the antibody binds to a protein retrieved from the database search.

8. The method of claim 7, wherein homologous sequences show at least 80% identity.

9. The method of claim 7, wherein the database comprises proteomes from bacteria, viruses, and eukaryotes.

10. The method of claim 1, wherein the identified peptide sequences binding to the antibody are hierarchically clustered and aligned.

11. The method of claim 1, further comprising examining peptides on the array that are not bound to antibody.

12. A method of characterizing binding specificity of an antibody, the method comprising the steps of:
   (a) contacting a sample comprising the antibody to a plurality of peptides immobilized on an array, wherein the array comprises at least 10,000 peptide features per 1 cm$^2$, wherein the peptides are spaced no more than 3 nm apart, wherein 95% of the peptides are in a range of 8 amino acids and 14 amino acids, and wherein the peptides are selected without a priori assuming a set of eliciting proteins or proteome;

(b) identifying peptides that bind to the antibody with a K$_d$ of less than 10$^{-7}$M;

(c) identifying peptides on the array that do not bind to the antibody; and (d) clustering and aligning the identified peptides from (b) and (c) to determine level of specific binding recognized by the antibody.

13. The method of claim 12, wherein the antibody is a monoclonal antibody.

14. The method of claim 13, wherein the identified peptides are clustered by similarity of the identified peptides in (b) and (c) to an eliciting peptide used to make the monoclonal antibody.

15. The method of claim 14, wherein the identified peptides are hierarchically clustered and aligned.

16. The method claim 14, wherein a level of similarity of identified peptides in steps (b) and (c) to the eliciting peptide is indicative of a degree of promiscuity of antibody binding.

17. The method of claim 12, wherein screening the peptide sequences of the identified peptides binding to an antibody in step (b) further comprises determining a consensus sequence motif.

18. The method of claim 17, wherein determining the consensus sequence comprises aligning the identified peptide sequences using a search algorithm.

* * * * *